(12) United States Patent
Umemoto et al.

(10) Patent No.: US 10,155,739 B2
(45) Date of Patent: Dec. 18, 2018

(54) HALOGENATED S-(PERFLUOROALKYL)DIBENZOTHIOPHENIUM SALT AND ITS PRODUCTION METHODS

(71) Applicant: Zhejiang Jiuzhou Pharmaceutical Co., Ltd., Taizhou (CN)

(72) Inventors: Teruo Umemoto, Taizhou (CN); Bin Zhang, Taizhou (CN); Tianhao Zhu, Taizhou (CN); Xiaocong Zhou, Taizhou (CN); Yuanqiang Li, Taizhou (CN)

( * ) Notice: Subject to any disclaimer, the term of this patent is extended or adjusted under 35 U.S.C. 154(b) by 0 days.

(21) Appl. No.: 15/539,145

(22) PCT Filed: Dec. 30, 2015

(86) PCT No.: PCT/CN2015/099798
§ 371 (c)(1),
(2) Date: Jun. 23, 2017

(87) PCT Pub. No.: WO2016/107578
PCT Pub. Date: Jul. 7, 2016

(65) Prior Publication Data
US 2017/0349567 A1    Dec. 7, 2017

(30) Foreign Application Priority Data

Dec. 31, 2014   (CN) .......................... 2014 1 0853220
Mar. 16, 2015   (CN) .......................... 2015 1 0112921

(51) Int. Cl.
*C07D 333/76*   (2006.01)
(52) U.S. Cl.
CPC .......... *C07D 333/76* (2013.01); *Y02P 20/582* (2015.11)
(58) Field of Classification Search
CPC ........................ C07D 333/76; Y02P 20/582
See application file for complete search history.

(56) References Cited

U.S. PATENT DOCUMENTS 5,066,795 A * 11/1991 Umemoto ............. C07C 45/511
540/1
2004/0265733 A1* 12/2004 Houlihan ............. G03F 7/0045
430/270.1

FOREIGN PATENT DOCUMENTS

| JP | 05339261 A | 12/1993 |
| JP | 10-182632 | * 7/1998 |
| JP | 10182632 A | 7/1998 |

OTHER PUBLICATIONS

Mace, Eur J Org Chem, 9(31), 1390-1397, 2009. (Year: 2009).*
Osamu Shimomura et al Journal of polymer science:part A:Polymer Chemistry vol. 38 year 2000.
Yohan Mace et al Eur.J.Org.Chem.,No. 9, year 2009,pp. 1390-1397.

* cited by examiner

*Primary Examiner* — D Margaret M Seaman

(57) ABSTRACT

Halogenated S-(perfluoroalkyl)dibenzothiophenium salt represented by the following general formula (I):

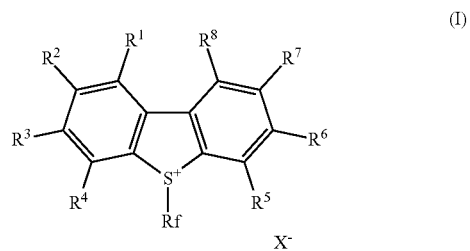

This compound is a new, reactive, and industrially useful reagent for perfluoroalkylating organic compounds. The reagent can be prepared by a one-pot process or a two-step reaction process from a halogenated biphenyl and easily isolated by a filtration method. In addition, the halogenated biphenyl can be recovered by desulfurization from a halogenated dibenzothiophene obtained as a side-product by the usage of the reagent.

20 Claims, No Drawings

HALOGENATED S-(PERFLUOROALKYL)DIBENZOTHIOPHENIUM SALT AND ITS PRODUCTION METHODS

This application claims the priority of China Patent Application No. 201410853220.9 and 201510112921.1 with the Patent Office of China on Dec. 31, 2014 and Mar. 16, 2015 successively titled "Halogenated S-(perfluoroalkyl)dibenzothiophenium salt and its production methods", the contents of which are incorporated herein by reference in their entirety.

FIELD OF THE INVENTION

The present inventions relate to new S-(perfluoroalkyl) dibenzothiophenium salt which is useful electrophilic perfluoroalkylating agent, and its production methods.

PRIOR ART

A perfluoroalkyl group is a very useful functional group because it has unique properties such as high electronegativity, high stability, and high lipophilicity (for example, see, P. Kirsch, "Modern Fluoroorganic Chemistry, Synthesis, Reactivity, Applications", Wiley-VCH Verlag GmbH & Co. KGaA, Weinheim, 2004). Among perfluoroalkyl groups, a low perfluoroalkyl group of one to four carbons, in particular, a trifluoromethyl group, is important for developing effective medicines, agrochemicals, and other useful materials. Thus, there have been developed many useful medicines and agrochemicals having trifluoromethyl groups (for example, see, K. L. Kirk, J. Fluorine Chem. 2006, 127, 1013-1029; S. Purser at al., Chem. Soc. Rev., 2008, 37, 237-432; G. Theodoridis, "Fluorine and the environment", Vol. 2, Chapter 4, pp 121-175 (2006) (ISSN 1872-0358)). Therefore, in order to improve their production processes and to make more effective medicines, agrochemicals, and others, there have been continued active research and development to make new methods for preparing the perfluoroalkylated organic compounds (for example, see, J.-A. Ma, D. Cahard, Journal of Fluorine Chemistry, 2007, 128, 975-996; G. K. S. Prakash, A. K. Yudin, Chem. Rev., 1997, 97, 757-786; T. Umemoto, Chem. Rev., 1996, 96, 1757-1778). Among them, electrophilic trifluoromethylating agents are particularly useful because they can directly trifluoromethylate nucleophilic organic molecules. Therefore, there have been reported many electrophilic trifluoromethylating agents to produce trifluoromethylated organic compounds (for example, see, S. Barata-Vallejo, B. Lantano, A. Postigo, Chem. Eur. J. 2014, 12, 16806-16829; Y. Macé, E. Magnier, Eur. J. Org. Chem. 2012, 2479-2494; N. Shibata at al., Beilstein J. Org. Chem., 2010, 6, No. 65).

Among the electrophilic trifluoromethylating reagents, S-(trifluoromethyl)dibenzothiophenium salts (A), which are called as Umemoto reagent, are particularly useful reagents for preparing trifluoromethylated organic compounds [for example, see, C. Zhang, Organic & Biomolecular Chemistry, 2014, 12, 6580-6589; H. Li, Synlett, 2012, 23, 2289-2290; T. Umemoto at al. J. Am. Chem. Soc., 1993, 115, 2156-2164 (1993)].

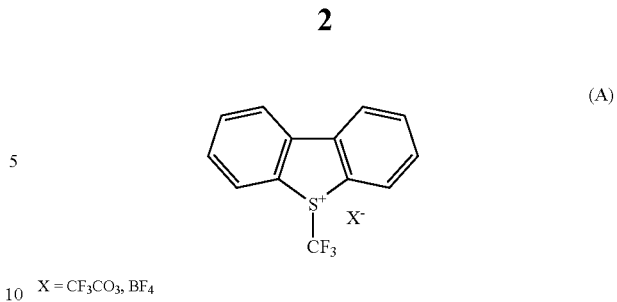

(A)

$X = CF_3CO_3, BF_4$

The alkyl and nitro derivatives, 2,8-dimethyl-S-(trifluoromethyl)dibenzothiophenium salts, 3,7-di-tert-butyl-S-(trifluoromethyl)dibenzothiophenium salts, 3-nitro-S-(trifluoromethyl)dibenzothiophenium salt, and 3,7-dinitro-S-(trifluoromethyl)dibenzothiophenium salt, and the corresponding selenium (Se) and tellurium (Te) salts were also developed (see, T. Umemoto et al., J. Am. Chem. Soc., 1993, 115, 2156-2164 (1993)). The zwitter-ion type of Umemoto reagents were also prepared (see, T. Umemoto at al., J. Fluorine Chem., 1995, 74, 77-82).

However, the practical preparative methods for the Umemoto reagent have significant problem, which requires multiple steps starting from 2-hydroxybiphenyl as a starting material as shown in Scheme 1: (step 1), reaction of 2-hydroxybiphenyl with dimethylthiocarbamoyl chloride; (step 2), isomerization by heating at high temperature; (step 3), hydrolysis with alkaline; (step 4), methylation with dimethyl sulfate; (step 5), chlorination with chlorine; (step 6), fluorination with triethylamine tris(hydrogen fluoride); (step 7), oxidation with hydrogen peroxide; (step 8), cyclization with fuming sulfuric acid; (step 9), exchange reaction of counteranion with sodium trifluoromethanesulfonate or sodium tetrafluoroborate (see, T. Umemoto at al., J. Fluorine Chem. 1999, 98, 75-81).

Scheme 1. Practical production process for Umemoto reagent (A)

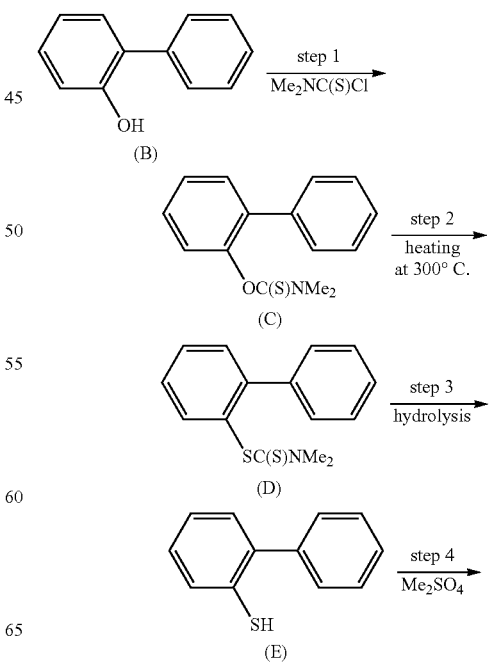

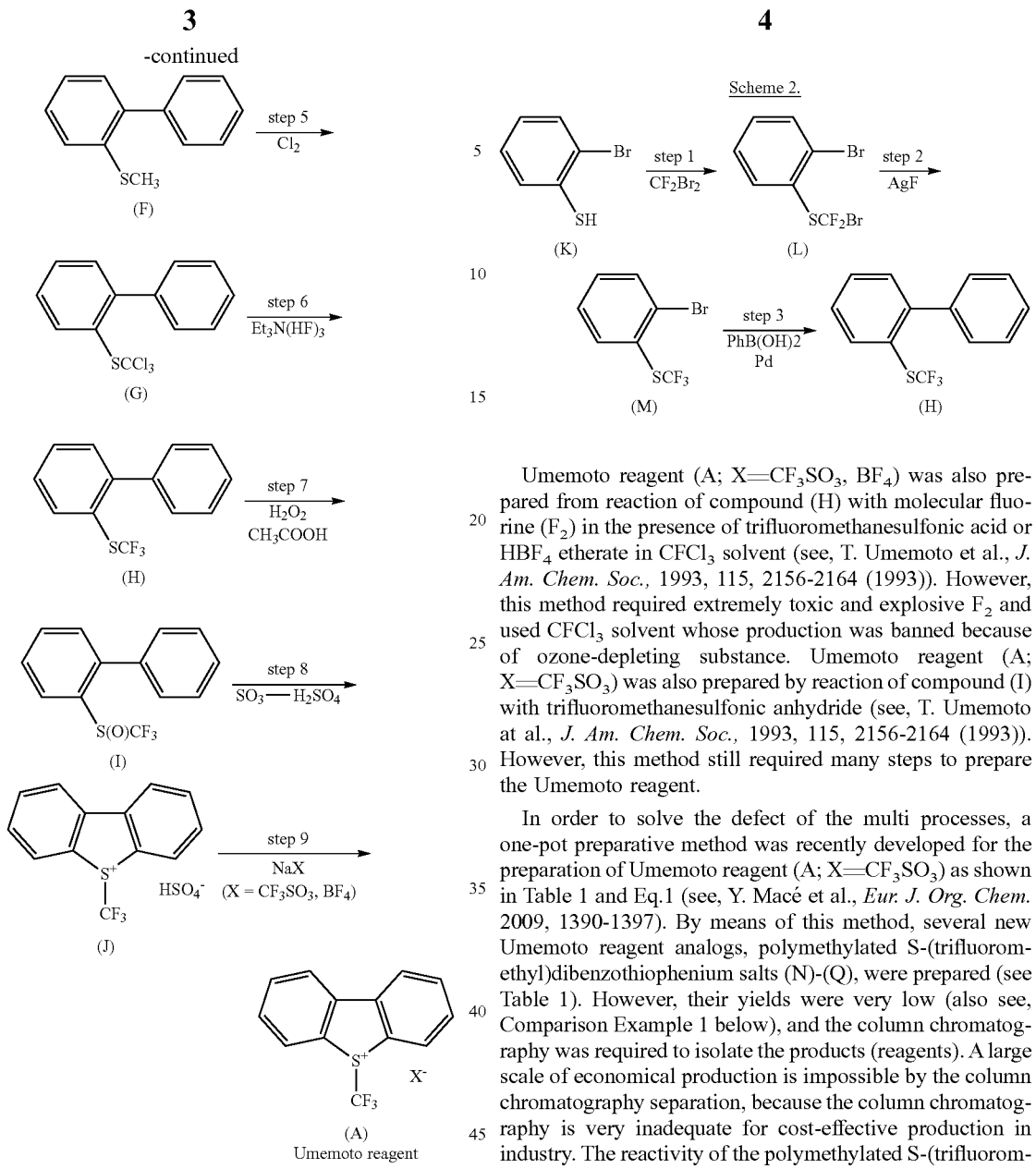

The shortcut process of compound (E) to compound (H) was reported, method of which was the conversion of compound (E) to its sodium salt (sodium biphenyl-2-yl thiolate) followed by the treatment with CF₃Br or CF₃I (see, T. Umemoto et al., *J. Fluorine Chem.*, 1999, 98, 75-81). However, this process required CF₃Br whose production was banned or regulated because of ozone-depleting substance or CF₃I that is expensive.

The intermediate compound (H) was also prepared by the following processes as shown in Scheme 2 (see, S. S. Aiken, J. A. H. Lainton, and D. A. Widdowson, *Electronic Conference on Trends in Organic Chemistry* 1995, (ECTOC-1), Eds H. S. Rzepa and J. M. Goodman (CD-ROM), RSC Publications, http://www.ch.ic.ac.uk/ectoc/papers/22/). However, this method required CF₂Br₂ which is regulated as one of ozone-depleting substances and very expensive AgF. This method also required multi-step processes for the production of Umemoto reagent.

Umemoto reagent (A; X=CF₃SO₃, BF₄) was also prepared from reaction of compound (H) with molecular fluorine (F₂) in the presence of trifluoromethanesulfonic acid or HBF₄ etherate in CFCl₃ solvent (see, T. Umemoto et al., *J. Am. Chem. Soc.*, 1993, 115, 2156-2164 (1993)). However, this method required extremely toxic and explosive F₂ and used CFCl₃ solvent whose production was banned because of ozone-depleting substance. Umemoto reagent (A; X=CF₃SO₃) was also prepared by reaction of compound (I) with trifluoromethanesulfonic anhydride (see, T. Umemoto at al., *J. Am. Chem. Soc.*, 1993, 115, 2156-2164 (1993)). However, this method still required many steps to prepare the Umemoto reagent.

In order to solve the defect of the multi processes, a one-pot preparative method was recently developed for the preparation of Umemoto reagent (A; X=CF₃SO₃) as shown in Table 1 and Eq.1 (see, Y. Macé et al., *Eur. J. Org. Chem.* 2009, 1390-1397). By means of this method, several new Umemoto reagent analogs, polymethylated S-(trifluoromethyl)dibenzothiophenium salts (N)-(Q), were prepared (see Table 1). However, their yields were very low (also see, Comparison Example 1 below), and the column chromatography was required to isolate the products (reagents). A large scale of economical production is impossible by the column chromatography separation, because the column chromatography is very inadequate for cost-effective production in industry. The reactivity of the polymethylated S-(trifluoromethyl)dibenzothiophenium salts is low, because the trifluoromethylating power of S-(trifluoromethyl)dibenzothiophenium salt is decreased by methyl substituents that are electron-donating groups. Electron-withdrawing substituents increase the trifluoromethylating power (see, T. Umemoto at al., *J. Am. Chem. Soc.*, 1993, 115, 2156-2164).

TABLE 1

A one-pot preparation of S-(trifluoromethyl)dibenzothiophenium salts, Umemoto reagent (A; X = CF₃SO₃) and its analogs (N)-(Q)

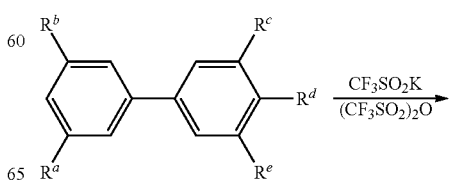

TABLE 1-continued

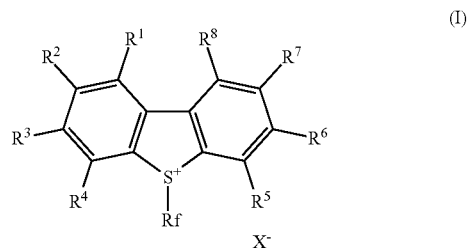

(Eq. 1)
(A), (N)-(Q)

| Product number | $R^a$ | $R^b$ | $R^c$ | $R^d$ | $R^e$ | Isolation method | Product yield (%) |
|---|---|---|---|---|---|---|---|
| (A) | H | H | H | H | H | Column chromato-graphy | 12% (Umemoto reagent) |
| (N) | H | $CH_3$ | $CH_3$(H) | H | H($CH_3$) | Column chromato-graphy | 15% |
| (O) | $CH_3$ | $CH_3$ | H | H | H | Column chromato-graphy | 36% |
| (P) | $CH_3$ | $CH_3$ | $CH_3$ | H | $CH_3$ | Column chromato-graphy | 46% |
| (Q) | $CH_3$ | $CH_3$ | H | $NO_2$ | H | Column chromato-graphy | 27% |

Most recently, another Umemoto analog, 2,4-dimethyl-7-pentafluorosulfanyl-S-(trifluoromethyl)dibenzothiophenium trifluoromethanesulfonate was prepared by the one-pot preparative method (see, T. Okazaki et al., *Journal of Fluorine Chemistry*, 2014, 165, 91-95). However, although the yield was a little better (55%), it also required the very low cost-effective column chromatography to isolate the product (reagent). In addition, it used an expensive starting material that was 3,5-dimethyl-4'-(pentafluorosulfanyl)biphenyl.

Umemoto reagent and its analogs have another significant drawback that, when they are used as perfluoroalkylating agents, they produce dibenzothiophene (R) or its analog as a byproduct in a quantitative yield or in a high yield in addition to the perfluoroalkylated compounds as illustrated in Scheme 3. The dibenzothiophene must be treated as a waste. This is a significant problem in current environmental issue.

Scheme 3.
Trifluoromethylation of nucleophilic organic compounds with Umemoto Reagent

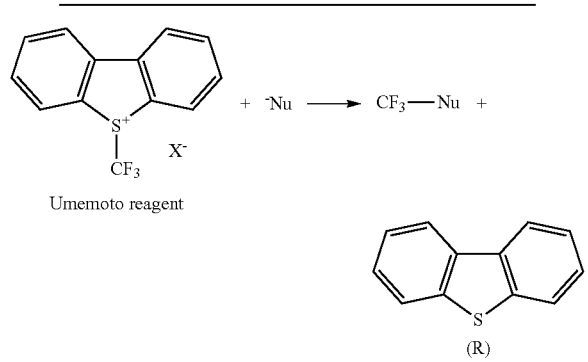

Nu = nucleophilic organic compounds

An ideal Umemoto agent must satisfy all the following subjects: (1) short step and high cost-effective production, (2) powerful perfluoroalkylating capability, (3) recycle of the dibenzothiophene obtained after the perfluoroalkylation. However, the current Umemoto reagent and Umemoto-type reagents have many serious shortcomings, because they do not satisfy the above subjects.

OBJECTS OF THE INVENTIONS

The present inventions are to provide a new halogenated S-(perfluoroalkyl)dibenzothiophenium salt which is useful as a powerful electrophilic perfluoroalkylating agent and to provide its cost-effective and green production methods.

CONSTITUENTS OF THE INVENTIONS

To solve the above-stated problems, the inventors have thoroughly studied an idea of making new and specified S-(perfluoroalkyl)dibenzothiophenium salt which can satisfy all the subjects stated above. As a consequence, they succeeded in making a new halogenated S-(perfluoroalkyl) dibenzothiophenium salt which can satisfy all the subjects.

The present invention relates to halogenated S-(perfluoroalkyl)dibenzothiophenium salt as presented by the following general formula (I) that is useful as a powerful electrophilic perfluoroalkylating agent.

General Formula (I):

(I)

(in the above general formula, Rf means a perfluoroalkyl group having 1 to 4 carbons; $R^1$, $R^2$, $R^3$, $R^4$, $R^5$, $R^6$, $R^7$ and $R^8$ each is a hydrogen atom or a halogen atom, provided that the total number of halogen atoms of $R^{1-8}$ is 1 to 5; and $X^-$ is a conjugated base of Brønsted acid)

In the above-stated general formula (I), specific examples for Rf are normal chain or branching perfluoroalkyl groups having 1 to 4 carbons, such as $CF_3$, $C_2F_5$, n-$C_3F_7$, iso-$C_3F_7$, n-$C_4F_9$, sec-$C_4F_9$, iso-$C_4F_9$, and tert-$C_4F_9$. Among them, $CF_3$, $C_2F_5$, and iso-$C_3F_7$ are preferable, and $CF_3$ is most preferable because it is the most significant functional group in the biochemical application such as medicines and agrochemicals.

In the above-stated general formula (I), a total number of halogen atoms of $R^{1-8}$ is one to five, and preferably two to four. The halogen atom is a fluorine, chlorine, bromine, or iodine atom, and preferably a fluorine or chlorine atom because of less molecular weight and higher electronegativity. Among them, a fluorine atom is the most preferable because of the smallest molecular weight and the highest electronegativity, and in addition, it can form the strongest carbon-fluorine (C—F) bond that is stable. The smallest molecular weight of fluorine makes the product more effective perfluoroalkylating agent per weight. The highest electronegativity makes the halogenated S-(perfluoroalkyl) dibenzothiophenium salt more powerful perfluoroalkylating agent. Therefore, the invented halogenated S-(perfluoroalkyl)dibenzothiophenium salts are more powerful than the Umemoto reagents (A) (see Examples 22-24 and Comparison Example 2 below). The strongest C—F bond makes it more effective to recover the fluorinated biphenyl from the dibenzothiophene obtained after the perfluoroalkylation by reduction reaction because of the high stability against the reduction reaction (see Examples 31 and 32 below).

In the above-stated general formula (I), X⁻ is a conjugated base of Brønsted acid (HX). The Brønsted acids include strong acids such as sulfuric acid, monomethyl sulfuric acid, chlorosulfonic acid, fluorosulfonic acid, methanesulfonic acid, trifluoromethanesulfonic acid, difluoromethanesulfonic acid, trichloromethanesulfonic acid, trifluoroethanesulfonic acid, perfluoroethanesulfonic acid, perfluorobutanesulfonic acid, benzenesulfonic acid, toluenesulfonic acid, nitrobenzenesulfonic acid, dinitrobenzenesulfonic acid, trifluoroacetic acid, trichloroacetic acid, hydrogen chloride (HCl), hydrogen bromide (HBr), $HBF_4$, $HBF_3Cl$, $HBFCl_3$, $HBCl_4$, $HSbF_6$, $HSbCl_5F$, $HSbCl_6$, $HAsF_6$, $HAlCl_4$, $HAlCl_3F$, $HAlF_4$, $HPF_6$, $HPF_5Cl$—, and $HClO_4$. Thus, as the conjugated bases (X⁻), $HSO_4^-$, $CH_3OSO_3^-$, $ClSO_3^-$, $FSO_3^-$, $CH_3SO_3^-$, $CF_3SO_3^-$, $CF_2HSO_3^-$, $CCl_3SO_3^-$, $CF_3CH_2SO_3^-$, $CF_2HCF_2SO_3^-$, $C_2F_5SO_3^-$, $C_3F_7SO_3^-$, $C_4F_9SO_3^-$, $C_6H_5SO_3^-$, $CH_3C_6H_4SO_3^-$, $O_2NC_6H_4SO_3^-$, $(O_2N)_2C_6H_3SO_3^-$, $CF_3CO_2^-$, $CCl_3CO_2^-$, $Cl^-$, $Br^-$, $BF_4^-$, $BF_3Cl^-$, $BF_3Cl_3^-$, $BCl_4^-$, $SbF_6^-$, $SbCl_5F^-$, $SbCl_6^-$, $AsF_6^-$, $AlCl_4^-$, $AlCl_3F^-$, $AlF_4^-$, $PF_6^-$, $PF_5Cl^-$, and $ClO_4^-$ are exemplified. Among them, preferably X⁻ is $CF_3SO_3^-$, $Cl^-$, $Br^-$, $BF_4^-$, $PF_6^-$, and $HSO_4^-$ because of easy access and high stability, and more preferably X⁻ is $CF_3SO_3^-$, $Cl^-$, and $BF_4^-$, and most preferably X⁻ is $CF_3SO_3^-$ because of the shortest production process (see Examples 1-7 below). When X⁻ is $Br^-$ or $HSO_4^-$, it may be exist as alcohol adduct or hydrate such as $Br^-$—$(CH_3OH)_n$ or $HSO_4^-$—$(H_2O)_n$ (n is positive number) (see Examples 10 and 14).

Preferred embodiments of formula (I) can be compounds represented by formula (Ia):

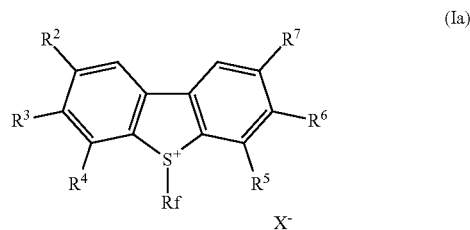

(in the above general formula of (Ia), Rf and X⁻ are the same as mentioned above, and $R^2$, $R^3$, $R^4$, $R^5$, $R^6$, and $R^7$ each is a hydrogen atom or a halogen atom, provided that the total number of halogen atoms of $R^{2-7}$ is 2 to 4)

In the above-stated general formula (Ia), a total number of halogen atoms of $R^{2-7}$ is two to four, and the halogen atom is a fluorine, chlorine, bromine, or iodine atom, and preferably a fluorine or chlorine atom because of less molecular weight and higher electronegativity. Among them, a fluorine atom is the most preferable because of the smallest molecular weight and the highest electronegativity, and in addition, it can form the strongest carbon-fluorine (C—F) bond that is stable. The smallest molecular weight of fluorine makes the product more effective perfluoroalkylating agent per weight. The highest electronegativity makes the halogenated S-(perfluoroalkyl)dibenzothiophenium salt more powerful perfluoroalkylating agent. Therefore, the invented halogenated S-(perfluoroalkyl)dibenzothiophenium salts are more powerful than the Umemoto reagents (A) (see Examples 22-24 and Comparison Example 2 below). The strongest C—F bond makes it more effective to recover the fluorinated biphenyl from the dibenzothiophene obtained after the perfluoroalkylation by reduction reaction because of the high stability against the reduction reaction (see Examples 31 and 32 below).

The invented compound shown by the following general formula (I') that has $X=CF_3SO_3$ in formula (I) can be produced in the process represented by the following Method 1 in Scheme 4.

Scheme 4.

Method 1

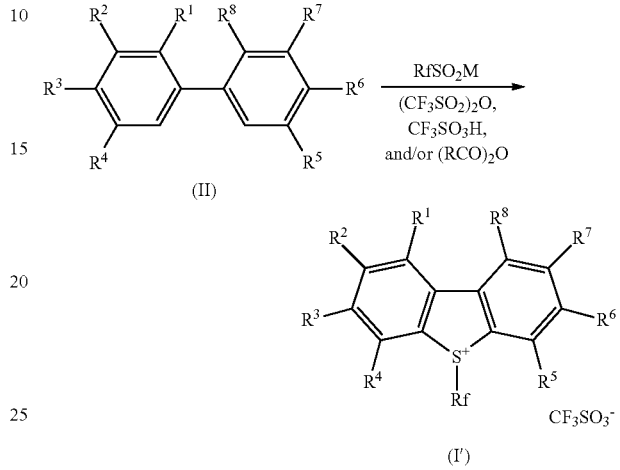

(in which Rf and $R^{1-8}$ are the same as mentioned above, and M is a metal or an ammonium moiety, and R is an alkyl or haloalkyl group having 1 to 4 carbons)

The method comprises reacting halogenated biphenyl represented by the general formula (II) with any combination of perfluoroalkanesulfinate salt represented by the general formula $RfSO_2M$ with trifluoromethanesulfonic anhydride $[(CF_3SO_2)_2O]$, trifluoromethanesulfonic acid $(CF_3SO_3H)$, and/or carboxylic anhydride represented by the general formula $(RCO)_2O$:

Preferably, the present invention includes methods which comprise reacting halogenated biphenyl represented by the general formula (II) with perfluoroalkanesulfinate salt represented by formula $RfSO_2M$ and trifluoromethanesulfonic anhydride (see, Scheme 5, Method 1a); reacting halogenated biphenyl of formula (II) with perfluoroalkanesulfinate salt represented by formula $RfSO_2M$, trifluoromethanesulfonic anhydride, and carboxylic anhydride represented by formula $(RCO)_2O$ (see, Scheme 5, Method 1b); reacting halogenated biphenyl represented by the general formula (II) with perfluoroalkanesulfinate salt represented by formula $RfSO_2M$, trifluoromethanesulfonic acid, and carboxylic anhydride represented by formula $(RCO)_2O$ (see, Scheme 5, Method 1c); reacting halogenated biphenyl represented by the general formula (II) with perfluoroalkanesulfinate salt represented by formula $RfSO_2M$, trifluoromethanesulfonic anhydride, trifluoromethanesulfonic acid, and carboxylic anhydride represented by formula $(RCO)_2O$ (see, Scheme 5, Method 1d);

Scheme 5.

Method 1a

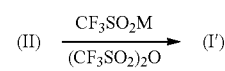

Process 1b

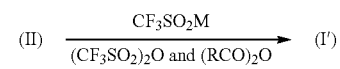

Method 1c

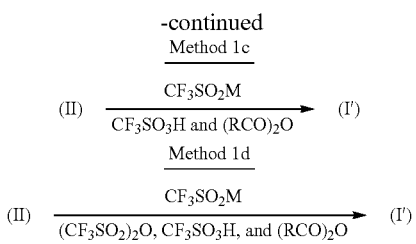

Method 1a can contain the process in which (first step) mixing perfluoroalkanesulfinate salt represented by the general formula RfSO$_2$M with trifluoromethanesulfonic anhydride and (second step) mixing halogenated biphenyl represented by the general formula (II) with a mixture of the first step.

Method 1a can also contain the process in which (first step) mixing perfluoroalkanesulfinate salt represented by the general formula RfSO$_2$M with trifluoromethanesulfonic anhydride and (second step) mixing a mixture of halogenated biphenyl represented by the general formula (II) and trifluoromethanesulfonic anhydride with a mixture of the first step.

The compound of the general formula (II) used in Method 1 is a known compound or the one that can be prepared easily by the known methods (for example, see, V. Penalva et al., Teterahedron Lett., 1998, 37, 2559-2560; Y. Ding at al, Tetrahedron Lett., 2012, 53, 6269-6272; B. Kaboudin at al., Synthesis, 2001, 91-96; J. Zhou at al., Journal of Chemical Research, 2012, 672-674; B. Kurscheid at al., Organometallics, 2012, 31, 1329-1334). Preferably, 3,3'-difluorobiphenyl, 4,4'-difluorobiphenyl, 3,4'-difluorobiphenyl, 3-fluoro-3'-chlorobiphenyl, 3,3'-dichlorobiphenyl, 4,4'-dichlorobiphenyl, 3,3',4-trifluorobiphenyl, 3,4,4'-trifluorobiphenyl, 3,3',5-trifluorobiphenyl, 3,4',5-trifluorobiphenyl, 3,3',4,4'-tetrafluorobiphenyl, 3,3',4,5'-tetrafluorobiphenyl, 3,3',5,5'-tetrafluorobiphenyl, 3,3',4,5-tetrafluorobiphenyl, 3,3',4,4',5-pentafluorobiphenyl, and 3,3',4,5,5'-pentafluorobiphenyl are exemplified, and more preferably 3,3'-difluorobiphenyl, 4,4'-difluorobiphenyl, and 3,3',4,4'-tetrafluorobiphenyl, 3,3',5,5'-tetrafluorobiphenyl are exemplified because of their easy availability and high reactivity, and 3,3'-difluorobiphenyl and 3,3',4,4'-tetrafluorobiphenyl are furthermore preferable because of easy and high effective production of the corresponding S-(perfluoroalkyl)dibenzothiophenium salts of formula (I').

The perfluoroalkanesulfinate salt of the general formula RfSO$_2$M used in Method 1 is commercially available or the one that can be prepared easily by the reported methods (see, R. N. Hazeldine at al., J. Chem. Soc., 1955, 2901-2910; M. Tordeux at al., J. Org. Chem., 1989, 54, 2452-2453; R. P. Singh at al., Chem, Commun., 2002, 1818-1819; H. W. Roesky at al., J. Fluorine Chem., 1976, 7, 77-84; B. R. Langlois et al., J. Fluorine Chem., 2007, 128, 851-856). As perfluroalkanesulfinate salts, metal salts or ammonium salts of perfluoroalkanesulfinic acids having one to four carbons can be used. As suitable metal, alkali metals, alkali earth metals, and transition metals are exemplified, and as suitable ammonium moiety, NH$_4$, CH$_3$NH$_3$, C$_2$H$_5$NH$_3$, (C$_2$H$_5$)$_3$NH, (CH$_3$)$_4$N, (C$_2$H$_5$)$_4$N, (C$_4$H$_9$)$_4$N are exemplified. Among them, alkali metal salts such as lithium trifluoromethanesulfinate, sodium trifluoromethanesulfinate, potassium trifluoromethanesulfinate, and cesium trifluoromethanesulfinate are more preferable because of its easy access. Sodium trifluoromethanesulfinate and potassium trifluoromethanesulfinate are furthermore preferable because of its commercial availability. The amount of the perfluoroalkanesulfinate salt of the formula RfSO$_2$M can be suitably decided in a range of about 0.5 mol to about 10 mol, or preferably about 1 mol to about 5 mol for 1 mol of the compound of formula (II).

Trifluoromethanesulfonic anhydride used in Method 1 is commercially available. The amount can be suitably decided in a range of about 0.5 mol to about 10 mol, or preferably about 1 mol to about 5 mol for 1 mol of perfluoroalkanesulfinate salt of formula RfSO$_2$M.

Trifluoromethanesulfonic acid used in Method 1 is commercially available. The amount can be suitably decided in a range of about 0.5 mol to about 20 mol, or preferably about 1 mol to about 15 mol for 1 mol of perfluoroalkanesulfinate salt of formula RfSO$_2$M.

Carboxylic anhydride represented by formula (RCO)$_2$O, in which R is an alkyl or haloalkyl group having 1 to 4 carbons, used in the Method 1 is commercially available. As an alkyl group, methyl, ethyl, propyl, isopropyl, butyl, sec-butyl, isobutyl, and tart-butyl are exemplified. As a haloalkyl group, chloromethyl, dichloromethyl, trichloromethyl, trifluoromethyl, and pentafluoroethyl are preferably exemplified. As carboxylic anhydride, acetic anhydride, chloroacetic anhydride, dichloroacetic anhydride, trichloroacetic anhydride, trifluoroacetic anhydride, propionic anhydride, pentafluoropropionic anhydride, butyric anhydride, and isobutyric anhydride are preferably exemplified. Among them, acetic anhydride and trifluoroacetic anhydride are more preferable because of availability and trifluoroacetic anhydride is most preferable because of high reactivity. The amount of the carboxylic anhydride can be suitably decided in a range of about 0.5 mol to about 20 mol, or preferably about 1 mol to about 15 mol for 1 mol of perfluoroalkanesulfinate salt of formula RfSO$_2$M.

The reactions of Method 1 can be conducted with or without solvent. As the solvent usable for the reaction, polar solvents such as nitromethane, nitroethane, 1-nitropropane, 2-nitropropane, nitrobenzene, sulfolane, 2-methylsulfolane, ethyl methyl sulfone, and so on; halocarbons such as dichloromethane, chloroform, carbon tetrachloride, dichloroethane, trichloroethane, and so on; carboxylic acids such as acetic acid, propionic acid, trifluoroacetic acid, perfluoropropionic acid, and so on; and mixtures of these solvents, can be preferably exemplified. Among them, the polar solvents such as nitromethane and sulfolane and the carboxylic acids such as trifluoroacetic acid are more preferable because of good yield of the product, and nitromethane is furthermore preferable because of its easy-to-handle neutral solvent and easy recovery due to its low boiling point.

The reaction temperature of Method 1 can be suitably selected from a range of about −50° C. to about +150° C., more suitably, about −10° C. to about +100° C. The reaction time can be suitably selected so that the reaction is completed. It can be from about 0.5 hrs to several days, preferably with a few days.

The reaction mechanism of Method 1a may be explained in the following way as shown in Scheme 6. Perfluoroalkanesulfinate salt reacts with trifluoromethanesulfonic anhydride to produce perfluoroalkanesulfinyl trifluoromethanesulfonate (III) [RfS(O)OSO$_2$CF$_3$] which can react with halogenated biphenyl of formula (II) to produce halogenated 2-[(perfluoroalkyl)sulfinyl)]biphenyl represented by the general formula (IV) as an intermediate; and then, the intermediate reacts with other perfluoroalkanesulfinyl trifluoromethanesulfonate and/or trifluoromethanesulfonic anhydride, which exist in the reaction mixture, to produce the final halogenated S-(perfluoroalkyl)dibenzothiophenium trifluoromethanesulfonate of formula (I').

Scheme 6. Reaction mechanism of Method 1a (a first stage)

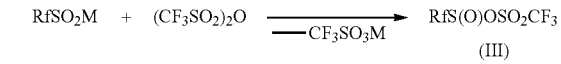

(a second stage)

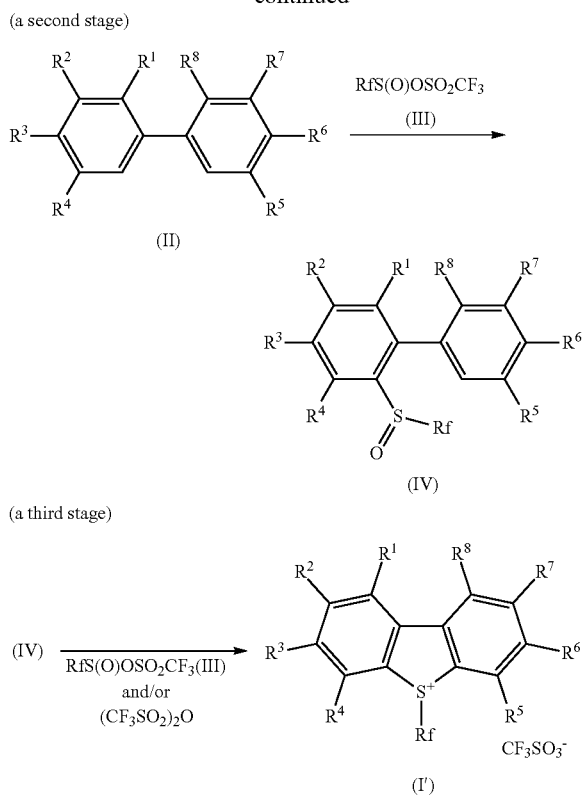

(a third stage)

(IV) $\xrightarrow[\text{and/or} \atop (CF_3SO_2)_2O]{RfS(O)OSO_2CF_3(III)}$ (I')

Actually, halogenated S-[(perfluoroalkyl)sulfinyl)]biphenyl represented by the general formula (IV) was detected as an intermediate in this invented reaction by $^{19}F$ NMR. For example, the $^{19}F$ NMR analysis of the intermediate reaction mixture in the reaction of 3,3'-difluorobiphenyl with sodium trifluoromethanesulfinate and trifluoromethanesulfonic anhydride showed a singlet signal of –73.24 ppm (—S(O) CF$_3$) which corresponded to 3,3'-difluoro-6-(trifluoromethylsulfinyl)biphenyl. The halogenated 2-[(perfluoroalkyl) sulfinyl]biphenyl represented by the general formula (IV) was synthesized by the reaction of halogenated biphenyl of formula (II) with sodium perfluoroalkanesulfinate and trifluoromethanesulfonic acid (see Example 15). It was also demonstrated that the intermediate halogenated 2-[(perfluoroalkyl)sulfinyl)]biphenyl represented by the general formula (IV) reacted with trifluoromethanesulfonic anhydride to give the halogenated S-(perfluoroalkyl)dibenzothiophenium salt of formula (I') (see Example 16). Thus, the present invention includes halogenated 2-[(perfluoroalkyl)sulfinyl] biphenyl represented by the general formula (IV) as an intermediate for the preparation of halogenated S-(perfluoroalkyl)dibenzothiophenium salt of formula (I).

The present invention also relates to the isolation method for halogenated S-(perfluoroalkyl)dibenzothiophenium trifluoromethanesulfonate of formula (I'). The method comprises washing the reaction mixture, which results from the reactions of halogenated biphenyl of formula (II) with the reactant(s) as mentioned above, with water and an organic solvent(s) which does not dissolve or scarcely dissolve the product, halogenated S-(perfluoroalkyl)dibenzothiophenium trifluoromethanesulfonate of formula (I'). When a solvent for the reaction is used, the reaction mixture may preferably be the reaction residue obtained after the evaporation of the solvent after the reaction. When a solvent for the reaction is not used, the reaction mixture may be the reaction mixture after the reaction. The reaction solvents are exemplified above.

The organic solvent for washing the reaction mixture does not dissolve or scarcely dissolve the product. As preferable organic solvents for washing the reaction mixture, ethers such as diethyl ether, dipropyl ether, di(isopropyl) ether, dibutyl ether, di(isobutyl) ether, di(sec-butyl) ether, tert-butyl methyl ether, 1,2-dimethoxyethane, 1,2-diethoxyethane, dioxane, diglyme, and so on; esters such as ethyl acetate, propyl acetate, isopropyl acetate, ethyl propionate, and so on; halocarbons such as methylene chloride, chloroform, carbon tetrachloride, dichloroethane, and so on; aromatics such as benzene, toluene, xylene, chlorobenzene, dichlorobenzene, fluorobenzene, benzotrifluoride, and so on; alkanes such as n-pentane, n-hexane, n-heptane, n-octane, and their steric isomers, and so on; and their mixtures, are exemplified. Among them, the ethers, the esters, the halocarbons, and the aromatics are exemplified more preferably. The reaction mixture may be washed with a mixture of water and the organic solvent. The reaction mixture may also be washed in a step-wise manner; it is washed with water and then with the organic solvent, or with the organic solvent and then with water. Washing with a mixture of water and the organic solvent is preferable because of shorter process number and production effectiveness. From the reaction mixture, water can remove byproducts which are trifluoromethanesulfonic acid and its salt, the carboxylic acid and its salt, and the starting material and reactants remained, which are trifluoromethanesulfinic acid and its salt, trifluoromethanesulfonic anhydride, trifluoromethanesulfonic acid, the carboxylic anhydride, and the carboxylic acid and its salt. Water can remove other compounds which dissolve in water. The organic solvents can remove the halogenated biphenyl remained and byproducts which are dissolved in the organic solvent(s). The organic solvents can remove other compounds which dissolve in the organic solvents. The product, halogenated S-(perfluoroalkyl)dibenzothiophenium trifluoromethanesulfonate of formula (I'), can easily be isolated only by washing the reaction mixture with water and the organic solvent(s) mentioned above without the column chromatography separation process.

Halogenated S-(Perfluoroalkyl)dibenzothiophenium salt of the general formula (I) can be prepared in the process represented in the following Method 2 as shown in Scheme 7.

Scheme 7.

Method 2

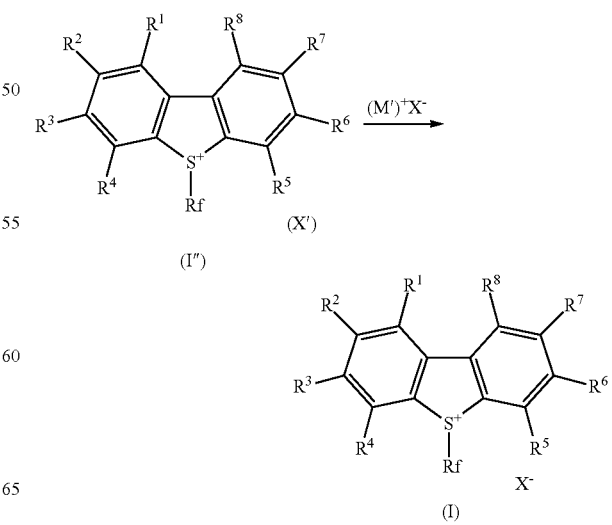

(in which Rf and $R^{1-8}$ are the same as above, M' is a hydrogen atom, a metal atom, or an ammonium moiety, and (X')⁻ and X⁻ each is a conjugated base of Brϕnsted acid (HX' or HX), provided that (X')⁻ and X⁻ are different)

This produces halogenated S-(perfluoroalkyl)dibenzothiophenium salt of the general formula (I) from another halogenated S-(perfluoroalkyl)dibenzothiophenium salt of formula (I'') by a counter-anion exchange reaction with (M')⁺X⁻.

[Method 2]

Halogenated S-(perfluoroalkyl)dibenzothiophenium salts with X'=CF₃SO₃ usable for this Method 2 can be prepared by Method 1 mentioned above. S-(Perfluoroalkyl)dibenzothiophenium salts having X' different from CF₃SO₃, usable for this Method 2, can be prepared from halogenated S-(perfluoroalkyl)dibenzothiophenium salts with X'=CF₃SO₃ by the counter-anion replacement reaction. As a preferable X', CF₃SO₃, Cl, Br, and HSO₄ are exemplified.

(M')⁺X⁻ are commercially available compounds or easily prepared by the conventional methods. As the (M')⁺X⁻, strong acids and their metal and ammonium salts are exemplified. The preferable strong acids include sulfuric acid, fluorosulfonic acid, chlorosulfonic acid, trifluoromethanesulfonic acid, perfluorobutanesulfonic acid, trichloromethanesulfonic acid, trifluoroacetic acid, trichloroacetic acid, HCl, HBr, HBF₄, HPF₆, HSbF₆, HAsF₆, HClO₄, and so on. The preferable metal and ammonium salts include CF₃SO₃Li, CF₃SO₃Na, CF₃SO₃K, CF₃SO₃Ag, CF₃SO₃NH₄, C₄F₉SO₃Na, (C₂H₅)₃NHCl, (CH₃)₄NCl, (C₂H₅)₄NCl, (C₄H₉)₄NCl, (C₄H₉)₄NBr, LiHSO₄, NaHSO₄, KHSO₄, AgHSO₄, (CH₃)₄NHSO₄, (C₂H₅)₄NHSO₄, (C₄H₉)₄NHSO₄, LiBF₄, NaBF₄, KBF₄, AgBF₄, NH₄BF₄, (C₂H₅)₃NHBF₄, (CH₃)₄NBF₄, (C₂H₅)₄NBF₄, (C₄H₉)₄NBF₄, LiPF₆, NaPF₆, KPF₆, AgPF₆, NH₄PF₆, (CH₃)₄NPF₆, (C₂H₅)₄NPF₆, (C₄H₉)₄NPF₆, LiSbF₆, NaSbF₅, KSbF₆, AgSbF₆, LiAsF₆, NaAsF₆, KAsSF₆, AgAsF₆, and so on.

This process can be preferably done with a solvent for smooth reaction and high yield. As a suitable solvent, a nitrile such as acetonitrile, propionitrile, and so on; a halocarbon such as dichloromethane, chloroform, carbon tetrachloride, dichloroethane, trichloroethane; an ether such as diethyl ether, tetrahydrofuran, dioxane, di(isopropyl) ether, tert-butyl methyl ether, dimethoxyethane, and so on; an aromatic compound such as benzene, toluene, chlorobenzene, benzotrifluoride, and so on; an alcohol such as methanol, ethanol, 2,2,2-trifluoroethanol, propanol, isopropanol, 1,1,1,3,3,3-hexafluoro-2-propanol, butanol, iso-butanol, sec-butanol, tert-butanol, and so on; water; and mixture of these solvents are exemplified.

The amount of (M')⁺X⁻ (M'=H) used in this reaction can be suitably decided in the range of about 1 mol to a large excess, preferably about 1 mol to about 10 mol, for 1 mol of the S-(perfluoroalkyl)dibenzothiophenium salt. The amount of (M')⁺X⁻ (M'=metal or ammonium moiety) can be suitably decided in the range of about 0.8 mol to about 2 mol, more preferably about 0.9 mol to about 1.5 mol, for 1 mol of the S-(perfluoroalkyl)dibenzothiophenium salt. The reaction temperature can be selected from a range of about 0° C. to about 100° C., preferably about room temperature to about 80° C. The reaction time can be selected so that the reaction is completed. It can be from about 10 min to a few days, preferably within a day.

This invention also relates to the reuse of halogenated dibenzothiophene represented by the following formula (V) which is obtained after the usage of the S-(perfluoroalkyl) dibenzothiophenium salt of formula (I) as a perfluoroalkylating agent.

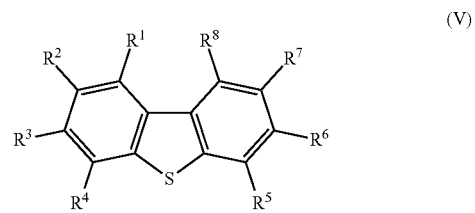

When the S-(perfluoroalkyl)dibenzothiophenium salt is used for perfluoroalkylation of an organic compound, halogenated dibenzothiophene of formula (V) is produced as a byproduct, which can be equimolar to the S-(perfluoroalkyl) dibenzothiophenium salt used, as seen in Scheme 8 (see reaction examples such as Examples 17, 21, and 27 below).

Scheme 8. Perfluoroalkylation of an organic compound with halogenated S-(perfluoroalkyl)dibenzothiophenium salt (I): Formation of halogenated dibenzothiophene (V)

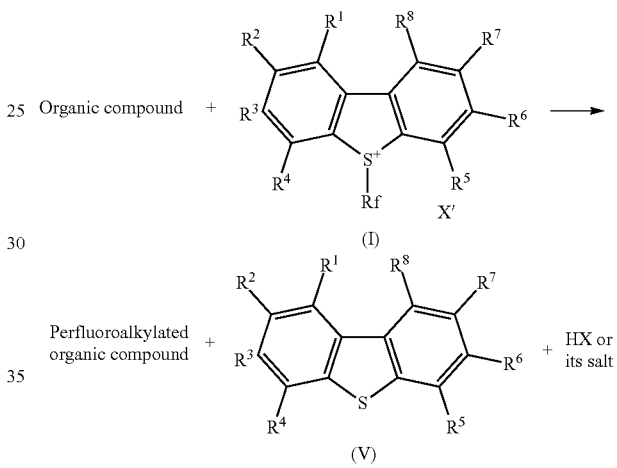

The halogenated dibenzothiophene of formula (V) can be reduced to produce halogenated biphenyl of formula (II) as shown in Scheme 9.

Scheme 9. Recovery of halogenated biphenyl (II) from halogenated dibenzothiophene (V)

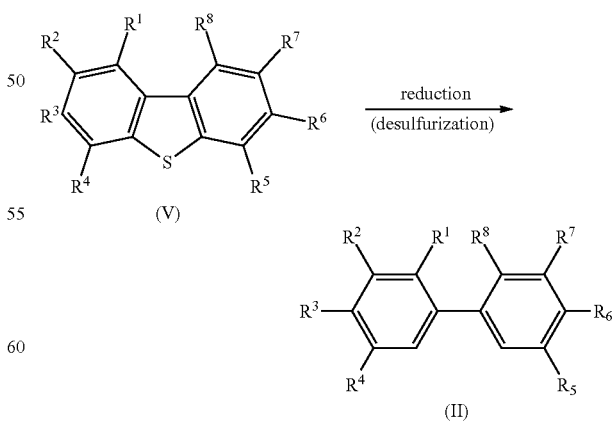

The reaction of Scheme 9 can be done by the reduction which are used for desulfurization of the sulfur compounds (see Examples 31 and 32 below). The halogenated biphenyl obtained by the desulfurization can be reused for the production of the halogenated S-(perfluoroalkyl)dibenzothiophenium salt of this invention.

The present invention also relates to the production of halogenated S-(perfluoroalkyl)dibenzothiophenium salt of formula (I) using halogenated biphenyl of formula (II), which is recovered by the reduction (desulfurization) of the halogenated dibenzothiophene of formula (V) obtained by the usage of the S-(perfluoroalkyl)dibenzothiophenium salt.

The production of halogenated S-(perfluoroalkyl)dibenzothiophenium salt can be done by means of Method 1 using the recovered halogenated biphenyl of formula (II). This can be done in the same way as described above except for the usage of the recovered halogenated biphenyl.

When halogenated S-(perfluoroalkyl)dibenzothiophenium trifluoromethanesulfonate of formula (I') ($X=CF_3SO_3$) is used as a perfluoroalkylating agent, trifluoromethanesulfonic acid or its salt is obtained in addition to a perfluoroalkylated organic compound and halogenated dibenzothiophene of formula (V). Trifluoromethanesulfonic anhydride can be prepared from the recovered trifluoromethanesulfonic acid or its salt by the conventional synthetic methods such as dehydration reaction with $P_2O_5$ (see, T. Gramstad, R. N. Haszeldine, *J. Chem. Soc.*, 1957, 4069-4079): $CF_3SO_3H + P_2O_5 \rightarrow (CF_3SO_2)_2O$.

INDUSTRIAL APPLICATION OF THE INVENTIONS

Halogenated S-(perfluoroalkyl)dibenzothiophenium salt represented by the above general formula (I) of the present invention is a useful electrophilic perfluoroalkylating agent of wide applications to prepare perfluoroalkylated organic compounds (see Examples 17-30 below).

The invented halogenated S-(perfluoroalkyl)dibenzothiophenium salt can be prepared by a very short process such as a one-pot process (see Examples 1-7 below) and isolated by a simple filtration of the products precipitated by washing the reaction mixture with water and an organic solvent (see Examples 1-5, and 7 below). These are highly useful for cost-effective production of the electrophilic perfluoroalkylating agent in industry.

In addition, as illustrated in Scheme 10, the halogenated biphenyl is recovered from the reduction (desulfurization) of the halogenated dibenzothiophene obtained from the usage of the halogenated S-(perfluoroalkyl)dibenzothiophenium salt for the perfluoroalkylation of organic compounds (see Examples 31 and 32). Another reactant, trifluoromethanesulfonic anhydride, may also be recovered from trifluoromethanesulfonic acid or salt obtained from the usage of the S-(perfluoroalkyl)dibenzothiophenium salt.

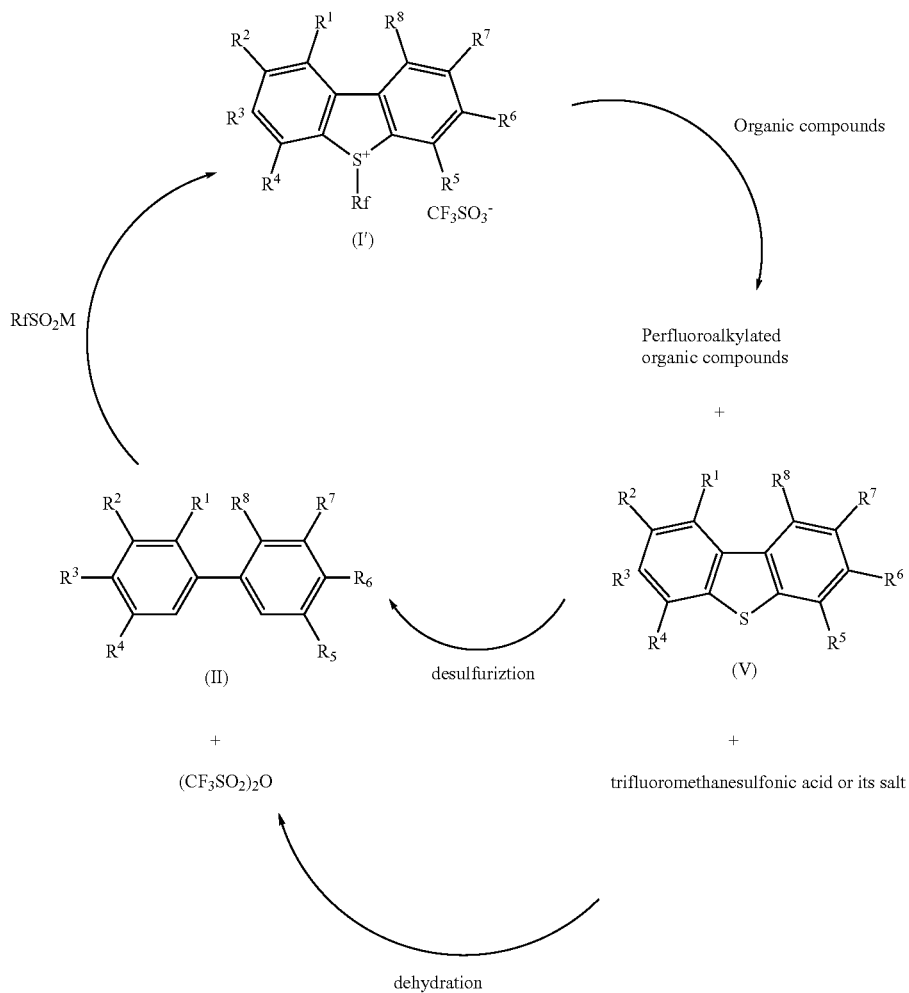

Scheme 10. Recycle system of halogenated S-(perfluoroalkyl)dibenzothiophenium salt The recycle as shown in Scheme 10 can provide a highly cost-effective and environmentally friendly (green) production of the halogenated S-(perfluoroalkyl)dibenzothiophenium salt and a highly cost-effective and environmentally friendly (green) production of the perfluoroalkylated organic compounds. Therefore, the present invention of the new halogenated S-(perfluoroalkyl)dibenzothiophenium salt and its production methods can provide a highly effective and environmentally friendly perfluoroalkylating agent that is industrially very important.

EMBODIMENTS (EXAMPLES)

Further details of the present inventions are provided through their embodiments below. The inventions shall, however, never be construed as restricted by these embodiments in any sense.

The numbering of the dibenzothiophene structure in nomenclature is shown in the following figure:

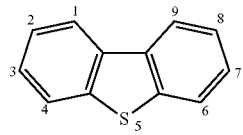

Example 1

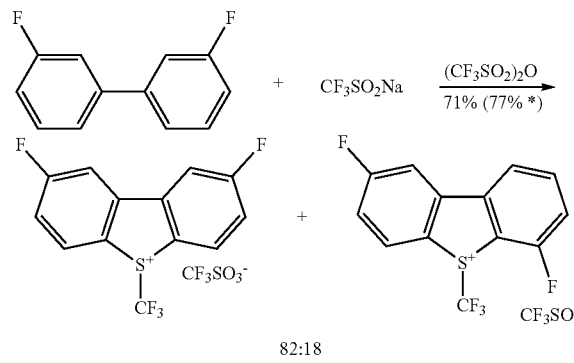

82:18

3,3'-Difluorobiphenyl (14.2 g, 74.7 mmol) was added to a stirred mixture of 14.0 g (90 mmol) of dried sodium trifluoromethanesulfinate and 100 mL of dry nitromethane under nitrogen atmosphere at room temperature (20° C.), and then the reactor was put on a water bath. After the mixture was stirred for 40 min, trifluoromethanesulfonic anhydride (50.6 g, 179.4 mmol) was added for 10 min and the reaction mixture was stirred at room temperature for 46 hrs. $^{19}$FNMR analysis of the reaction solution using benzotrifluoride as a standard showed that 8% of the starting material, 3,3'-difluorobiphenyl, remained unreacted and the products, 2,8-difluoro-S-(trifluoromethyl)dibenzothiophenium trifluoromethanesulfonate and 2,6-difluoro-S-(trifluoromethyl)dibenzothiophenium trifluoromethanesulfonate, were produced in 58% (63%*) and 13% (14%*) yields, respectively. The total yield was 71% (77%*). After the reaction solution was evaporated to dryness, 30 ml of dichloromethane was added to the residue and the solvent was evaporated up. Into the residue, 100 ml of water and 125 ml of dichloromethane were added and the mixture was stirred for 45 min. The resulting precipitates were collected by filtration, giving 20.1 g [61% (66%*)] of a 87:13 mixture of 2,8-difluoro-5-(trifluoromethyl)dibenzothiophenium trifluoromethanesulfonate and 2,6-difluoro-S-(trifluoromethyl)dibenzothiophenium trifluoromethanesulfonate as crystalline solid. The yields with *symbol were calculated based on the consumed starting material.

2,8-Difluoro-S-(trifluoromethyl)dibenzothiophenium trifluoromethanesulfonate was obtained as pure crystals by recrystallization: decomposition-starting point 204° C. (by TGA/DSC) (recrystallized from CH$_3$CN-diethyl ether); $^{19}$F NMR with $^1$H-irradiation (376.5 MHz, DMSO-d$_6$) δ −53.25 (3F, s, CF$_3$), −77.78 (3F, s, SO$_2$CF$_3$), −101.81 (2F, s, 2,8-F); $^1$H-NMR (400.2 MHz, DMSO-d$_6$) δ 8.76 (2H, dd, J=9.0, 4.8 Hz, 4,6-H), 8.56 (2H, dd, J=8.8, 2.8 Hz, 1,9-H), 7.84 (2H, dt, J=2.8, 9.0 Hz, 3,7-H); $^{13}$C-NMR (100.6 MHz, DMSO-d$_6$) δ 166.9 (d, J=261.6 Hz), 143.8 (dd, J=11.6, 2.5 Hz), 132.9 (d, J=10.1 Hz), 123.4 (quartet, J=332.3 Hz), 123.0 (d, J=2.0 Hz), 121.1 (quartet, J=321.9 Hz), 120.1 (d, J=24.1 Hz), 113.7 (d, J=27.2 Hz); IR (KBr) 3112, 3057, 1593, 1584, 1583, 1263, 1237, 1178, 1157, 1090, 1029, 903, 838, 757, 636, 571, 517, 492, 465 cm$^{-1}$; Mass spectrometry (ESI method) m/z, 289 (M$^+$—OSO$_2$CF$_3$); High resolution mass spectrum (ESI method) calcd for C$_{13}$H$_6$F$_5$S (M—OSO$_2$CF$_3$)$^+$, 289.0110. Found 289.0129. Elemental analysis: Calcd for C$_{14}$H$_6$F$_8$O$_3$S$_2$: C, 38.36%; H, 1.38%. Found: C, 38.45%; H. 1.67%.

2,6-Difluoro-S-(trifluoromethyl)dibenzothiophenium trifluoromethanesulfonate was identified by the NMR analysis of the mixture: $^{19}$F NMR with $^1$H-irradiation (376.5 MHz, DMSO-d$_6$) δ −52.46 (3F, d, J=6.6 Hz, CF$_3$), −77.78 (s, CF$_3$SO$_2$), −100.77 (1F, s, 2-F), −108.23 (1F, quartet, J=6.6 Hz, 6-F).

Pure 2,6-difluoro-S-(trifluoromethyl)dibenzothiophenium trifluoromethanesulfonate was isolated from another reaction by the following way. The reaction mixture was evaporated to dryness and the resulting residue was mixed by water and dichloromethane. The resulting precipitates were removed by filtration and the filtrate was concentrated and the residue was chromatographed on silica gel using a 10:1 mixture of dichloromethane and methanol as an eluent to give pure 2,6-difluoro-S-(trifluoromethyl)dibenzothiophenium trifluoromethanesulfonate as a crystalline solid: decomposition-starting point 135° C. (by TGA/DSC) (recrystallized from CH$_3$CN-diethyl ether); $^{19}$F NMR with $^1$H-irradiation (376.5 MHz, DMSO-d$_6$) δ −52.45 (3F, d, J=6.6 Hz, CF$_3$), −77.78 (s, CF$_3$SO$_2$), −100.76 (1F, s, 2-F), −108.23 (1F, quartet, J=6.6 Hz, 6-F); $^1$H NMR (400.2 MHz, DMSO-d$_6$) δ 8.77 (1H, dd, J=4.6, 8.9 Hz, 4-H), 8.67 (1H, dd, J=2.6, 8.9 Hz, 1-H), 8.47 (1H, d, J=8.4 Hz, 9-H), 8.26 (1H, dt, J=5.2, 8.4 Hz, 8-H), 7.95 (1H, t, J=8.4 Hz, 7-H), 7.88 (1H, dt, J=2.6, 8.9 Hz, 3-H); $^{13}$C NMR (100.6 MHz, DMSO-d$_6$) δ 167.3 (d, J=255.9 Hz, 2-C), 159.5 (d, J=257.5 Hz, 6-C), 144.1 (dd, J=11.2, 1.9 Hz), 143.0 (d, J=2.5 Hz), 140.2 (d, J=8.3 Hz), 133.2 (d, J=10.8 Hz), 123.5 (quartet, J=333.1 Hz, CF$_3$), 122.5 (d, J=2.8 Hz), 121.1 (quartet, J=322.2 Hz, SO$_2$CF$_3$), 120.8 (d, J=2.1 Hz), 120.6 (d, J=24.8 Hz), 119.7 (d, J=18.0 Hz), 114.5 (d, J=26.8 Hz), 113.3 (d, J=17.1 Hz); IR (KBr) 3059, 1603, 1583, 1490, 1474, 1447, 1267, 1224, 1169, 1155, 1103, 1075, 1027, 904, 838, 815, 804, 758, 733, 665, 634, 573, 516, 495, 454, 435, 404 cm$^{-1}$. Elemental analysis: Calcd for C$_1$H$_6$F$_8$O$_3$S$_2$: C, 3836%; H, 1.38%. Found: C, 38.28%; H, 1.45%.

The products of this invention were obtained and easily isolated by simple filtration from the reaction mixture in good yield. The filtration procedure is particularly useful for the economical industrial large scale production.

Example 2

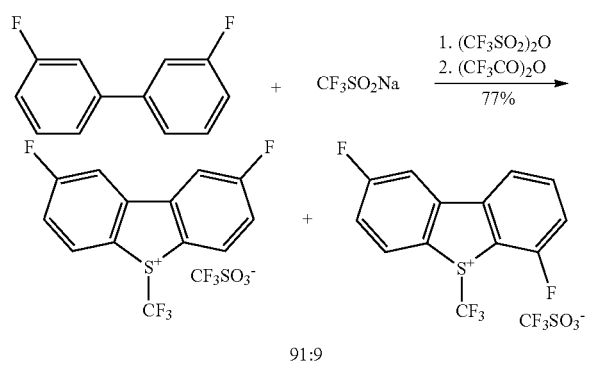

91:9

3,3'-Difluorobiphenyl (28.3 g 149 mmol) was added to a stirred mixture of 32.9 g (211 mmol) of dried sodium trifluoromethanesulfinate and 100 mL of dry nitromethane under nitrogen atmosphere at room temperature, and then the reactor was put on an ice bath. Trifluoromethanesulfonic anhydride (65.1 g, 231 mmol) was added for 40 min and then the reaction mixture was stirred for 2 hrs on an ice bath. After that, the ice bath was removed and the reaction mixture was stirred at room temperature for 3 hrs. Trifluoroacetic anhydride (37.8 g, 180 mmol) was then added and the reaction mixture was stirred 17 hrs at room temperature. After the reaction solution was evaporated to dryness, 130 mL of toluene was added to the residue and the solvent was evaporated up. Into the residue, 130 ml of water and 130 ml of toluene were added and the mixture was stirred for 20 min. The resulting precipitates were collected by filtration, giving 50.4 g (77%) of a 91:9 mixture of 2,8-difluoro-S-(trifluoromethyl)dibenzothiophenium trifluoromethanesulfonate and 2,6-difluoro-S-(trifluoromethyl)dibenzothiophenium trifluoromethanesulfonate as solid. The physical and spectral data of each of the products are shown in Example 1.

Example 3

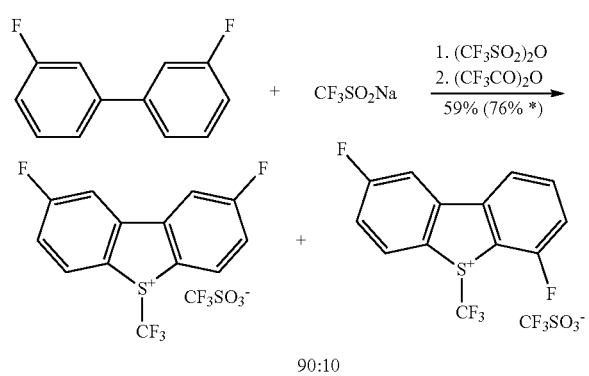

90:10

3,3'-Difluorobiphenyl (28.4 g, 149.5 mmol) was added to a stirred mixture of 25.3 g (162 mmol) of dried sodium trifluoromethanesulfinate and 100 mL of dry nitromethane under nitrogen atmosphere at room temperature, and then the reactor was put on a water bath. After the mixture was stirred for 35 min, trifluoromethanesulfonic anhydride (49.9 g, 177 mmol) was added for 10 min and then the reaction mixture was stirred for 30 min. Trifluoroacetic anhydride (37.2 g, 177 mmol) was added by one portion and the water bath was removed. The reaction mixture was stirred at room temperature for 22 hrs. $^{19}$FNMR analysis of the reaction solution using benzotrifluoride as a standard showed that 22% of the starting material 3,3'-difluorobiphenyl remained unreacted and the products, 2,8-difluoro-S-(trifluoromethyl)dibenzothiophenium trifluoromethanesulfonate and 2,6-difluoro-S-(trifluoromethyl)dibenzothiophenium trifluoromethanesulfonate, were produced in 53% (68%*) and 6% (8%*) yields, respectively [total 59% (76%*) yield]. The reaction solution was evaporated to dryness. Then 50 ml of toluene was added to the residue and the toluene was evaporated up. This operation was repeated again. Then 100 ml of water was added and the mixture was stirred for about 5 min. The resulting precipitates were collected by filtration, giving 36.3 g [55% (71%*) yield] of a 92:8 mixture of 2,8-difluoro-S-(trifluoromethyl)dibenzothiophenium trifluoromethanesulfonate and 2,6-difluoro-S-(trifluoromethyl)dibenzothiophenium trifluoromethanesulfonate as crystalline solid. The yields with *signal were calculated based on the consumed starting material 3,3'-difluorobiphenyl. The physical and spectral data of the products are shown in Example 1.

Example 4

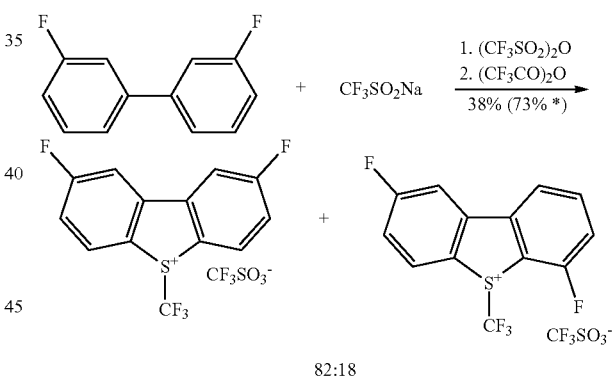

82:18

3,3'-Difluorobiphenyl (14.2 g, 74.7 mmol) was added to a stirred mixture of 15.2 g (97.4 mmol) of dried sodium trifluoromethanesulfinate and 100 mL of dry nitromethane under nitrogen atmosphere at room temperature, and then the reactor was put on a water bath. After stirring for 20 min, trifluoromethanesulfonic anhydride (29.5 g, 105 mmol) was added for 6 min. After stirring for 50 min, acetic anhydride (9.9 g, 97 mmol) was added by one portion. After stirring for 47 min, the water bath was removed and the reaction mixture was stirred at room temperature for 46 hrs. $^{19}$FNMR analysis of the reaction solution using benzotrifluoride as a standard showed that 49% of the starting material 3,3'-difluorobiphenyl remained unreacted and the products, 2,8-difluoro-S-(trifluoromethyl)dibenzothiophenium trifluoromethanesulfonate and 2,6-difluoro-S-(trifluoromethyl)dibenzothiophenium trifluoromethanesulfonate, were produced in 31% (60%*) and 7% (13%*) yields [total 38% (73%*)], respectively. The reaction solution was evaporated to dryness. Then, 50 mL of toluene was added to the residue and the toluene was evaporated up. This operation was repeated again. Then 100 mL of water was added and the mixture was stirred for 45 min. The resulting precipitates were collected by filtration, washed with 100 ml of toluene, and dried to give 11.7 g [36% (71%*)] yield] of a 86:14 mixture of 2,8-difluoro-S-(trifluoromethyl)dibenzothiophenium trifluoromethanesulfonate and 2,6-difluoro-5-(trifluoromethyl)dibenzothiophenium trifluoromethanesulfonate as crystalline solid. The yields with *signal were calculated based on the consumed starting material 3,3'-difluorobiphenyl. The physical and spectral data of the products are shown in Example 1.

Example 5

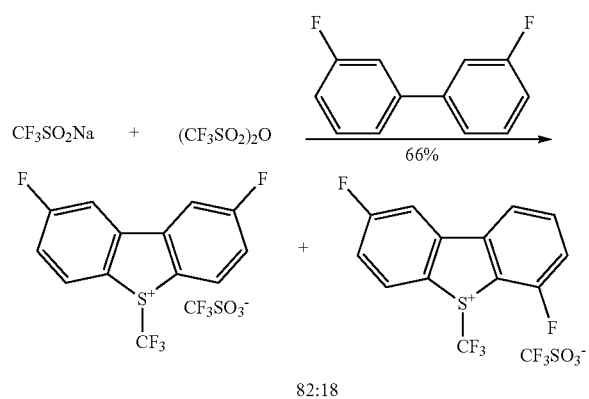

Trifluoromethanesulfonic anhydride (60.8 g, 216 mmol) was added to a stirred mixture of 28.1 g (180 mmol) of dried sodium trifluoromethanesulfinate and 200 mL of dry nitromethane under nitrogen atmosphere at ice bath temperature. The mixture was stirred for 5 hr at room temperature. After that, 11.4 g (60 mmol) of 3,3'-difluorobiphenyl was added to the mixture, and the mixture was stirred for 41 hrs at room temperature. $^{19}$F NMR analysis of the reaction solution using benzotrifluoride as a standard showed that the products, 2,8-difluoro-S-(trifluoromethyl)dibenzothiophenium trifluoromethanesulfonate and 2,6-difluoro-S-(trifluoromethyl)dibenzothiophenium trifluoromethanesulfonate were produced in 54% and 12% yields, respectively (total 66% yield). After the reaction, the reaction solution was evaporated to dryness, and then 100 mL of water and 100 mL of dichloromethane were added and the mixture was stirred for about 30 min. The resulting precipitates were collected by filtration, giving 15.0 g (57% yield) of a 93:7 mixture of 2,8-difluoro-S-(trifluoromethyl)dibenzothiophenium trifluoromethanesulfonate and 2,6-difluoro-S-(trifluoromethyl)dibenzothiophenium trifluoromethanesulfonate as crystalline solid. The physical and spectral data of the products are shown in Example 1.

Example 6

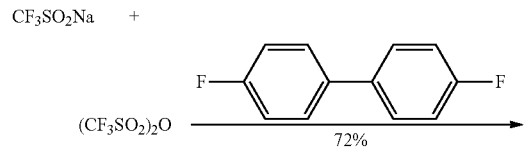

-continued

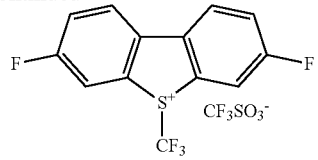

Trifluoromethanesulfonic anhydride (6.08 g, 21.6 mmol) was added to a stirred mixture of 2.81 g (18 mmol) of dried sodium trifluoromethanesulfinate and 15 mL of dry sulfolane under nitrogen atmosphere at room temperature. The mixture was stirred for 24 hrs at room temperature. After that, a solution of 1.14 g (6.0 mmol) of 4,4'-difluorobiphenyl in 5 mL of dry sulfolane was added to the mixture, and the mixture was stirred for 23 hrs at room temperature. $^{19}$F NMR analysis of the reaction solution using benzotrifluoride as a standard showed that 3,7-difluoro-S-(trifluoromethyl)dibenzothiophenium trifluoromethanesulfonate was produced in 72% yield. The product was isolated by the standard post-treatment using column chromatography. Its spectral data and physical properties are shown in the following: decomposition-starting point 164° C. (by TGA/DSC) (recrystallized from CH$_3$CN-diethyl ether); $^{19}$F NMR with $^1$H-irradiation (376.5 MHz, DMSO-d$_6$) δ −52.10 (3F, s, CF$_3$S), −77.78 (3F, s, CF$_3$SO$_2$), −107.03 (2F, s, 3,7-F); $^1$H NMR (400.2 MHz, DMSO-d$_6$) δ 8.59-8.62 (4H, m. 1,4,6, 9-H), 8.01 (2H, dt, J=2.4, 8.8 Hz, 2,8-H); $^{13}$C NMR (100.6 MHz, DMSO-d$_6$) δ 162.7 (d, J=252.0 Hz), 137.5 (s), 128.5 (d, J=11.6 Hz), 127.1 (d, J=9.3 Hz), 123.8 (d, J=23.0 Hz), 123.4 (quartet, J=333.3 Hz), 121.2 (quartet, J=322.5 Hz), 117.8 (d, J=29.1 Hz); IR (KBr) 3096, 1595, 1467, 1269, 1232, 1215, 1069, 1034, 873, 841, 758, 694, 575, 516, 459 cm$^{-1}$; High resolution mass spectrum (ESI method) Calcd for C$_{13}$H$_6$F$_5$S (M—OSO$_2$CF$_3$) 289.0110. Found 289.0116. Elemental analysis: Calcd for C$_{14}$H$_6$F$_8$O$_3$S$_2$: C, 38.36%; H, 1.38%. Found: C, 38.40%; H, 1.43%.

Example 7

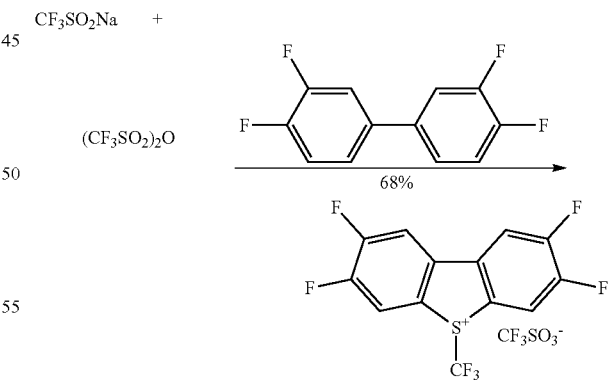

Trifluoromethanesulfonic anhydride (30.4 g, 108 mmol) was added to a stirred mixture of 14.1 g (90.4 mmol) of dried sodium trifluoromethanesulfinate and 70 mL of dry nitromethane under nitrogen atmosphere at ice bath cooling. The mixture was stirred for 6 hrs at room temperature. After that, a solution of 6.8 g (30.1 mmol) of 3,3',4,4'-tetrafluorobiphenyl in 30 ml of dry nitromethane was added to the mixture, and the mixture was stirred for 43 hrs at room temperature. $^{19}$F NMR of the reaction solution using benzotrifluoride as a standard showed that the product, 2,3,7,8-tetrafluoro-S-(trifluoromethyl)dibenzothiophenium trifluoromethanesulfonate was produced in 68% yield. After the reaction, the reaction solution was evaporated to dryness, and then 100 mL of water and 125 ml of dichloromethane were added and the mixture was stirred for 80 min. The resulting precipitates were collected by filtration, giving 8.3 g (58% yield) of 2,3,7,8-tetrafluoro-S-(trifluoromethyl)dibenzothiophenium trifluoromethanesulfonate as crystalline solid. The spectral data and physical properties are shown in the following: decomposition-starting point 171° C. (by TGA/DSC) (recrystallized from CH$_3$CN-diethyl ether); $^{19}$F NMR with $^1$H-irradiation (376.5 MHz, DMSO-d$_6$) δ −51.48 (3F, s, CF$_3$S), −77.82 (3F, s, CF$_3$SO$_2$), −124.89 (2F, d, J=21.5 Hz, 2,8-F), −129.47 (2F, d, J=21.5 Hz, 3,7-F); $^1$H NMR (400.2 MHz, DMSO-d$_6$) δ 8.81 (2H, dd, J=8.8, 7.2 Hz, 4,6-H), 8.72 (2H, dd, J=10.2, 7.0 Hz, 1,9-H); $^{13}$C NMR (100.6 MHz, DMSO-d$_6$) δ 155.0 (dd, J=257.4, 13.2 Hz), 151.0 (dd, J=255.7, 14.2 Hz), 138.4 (d, J=10.5 Hz), 123.5 (d, J=7.5 Hz), 123.2 (quartet, J=333.7 Hz), 121.1 (quartet, J=322.5 Hz), 120.1 (d, J=24.2 Hz), 115.2 (d, J=22.0 Hz); IR (KBr) 3102, 3038, 1608, 1493, 1438, 1277, 1256, 1242, 1224, 1172, 1073, 1029, 1001, 882, 784, 756, 639, 573, 521, 455 cm$^{-1}$: High resolution mass spectrum (ESI method) calcd for [C$_{13}$H$_4$F$_7$S]$^-$ (M—OSO$_2$CF$_3$)$^+$ 324.9922. Found 324.9926. Elemental analysis: Calcd for C$_{14}$H$_4$F$_{10}$O$_3$S$_2$: C, 35.45%; H, 0.85%. Found: C, 35.65%; H, 0.88%.

The product of this invention was obtained and easily isolated by simple filtration from the reaction mixture in good yield. The filtration procedure is particularly useful for the economical industrial large scale production.

Comparison Example 1

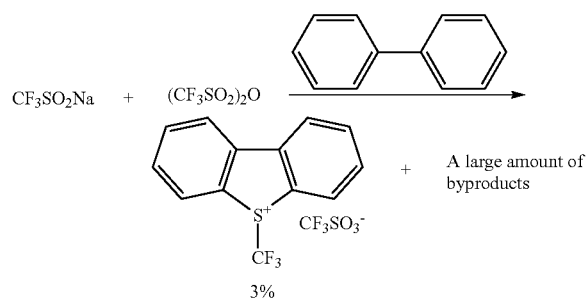

Trifluoromethanesulfonic anhydride (6.08 g, 21.6 mmol) was added to a stirred mixture of dried sodium trifluoromethanesulfinate (2.81 g, 18 mmol) and dry nitromethane (15 mL) at room temperature under nitrogen atmosphere. After the mixture was stirred for 3 hrs, a solution of biphenyl (0.93 g, 6.0 mmol) in dry nitromethane (5 mL) was added, and the mixture was stirred for 60 hrs at room temperature. $^{19}$F NMR analysis of the reaction solution using benzotrifluoride as a standard showed that S-(trifluoromethyl)dibenzothiophenium trifluoromethanesulfonate (Umemoto reagent) was produced in only 3% yield and a large amount of byproducts were produced.

As described above, the preparation of Umemoto reagent, S-(trifluoromethyl)dibenzothiophenium trifluoromethanesulfonate, was attempted using biphenyl in place of 3,3'-difluorobiphenyl in the same way as in Example 1. However, only 3% of the Umemoto reagent was produced and a large amount of byproducts were produced. In contrast, as exemplified in the Examples 1-7, the specified halogenated S-(perfluoroalkyl)dibenzothiophenium salts invented by the present invention are prepared in good yields. Accordingly, the invented compounds are particular useful, compared to the previous Umemoto reagent.

Example 8

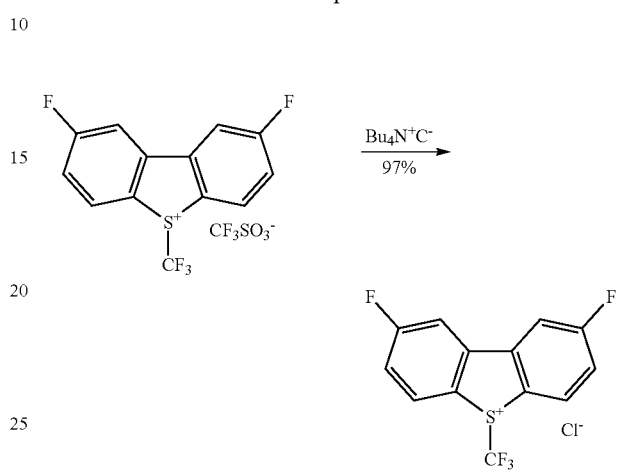

A solution of 2.54 g (9.15 mmol) of tetrabutylammonium chloride in 10 mL of acetonitrile was added into a stirred solution of 4.0 g (9.13 mmol) of 2,8-difluoro-S-(trifluoromethyl)dibenzothiophenium trifluoromethanesulfonate in 120 mL of acetonitrile. After the mixture was stirred overnight, the resulting precipitate was filtered to give 2.88 g (97%) of 2,8-difluoro-S-(trifluoromethyl)dibenzothiophenium chloride. The properties and spectral data are shown in the following: decomposition-starting point 230° C. (by TGA/DSC) (recrystallized from MeOH-Et$_2$O); $^{19}$F NMR with 11 irradiation (376.5 MHz, DMSO-d$_6$) δ −53.51 (3F, s, CF$_3$), −102.80 (2F, s, 2,8-F); $^1$H NMR (400.2 MHz, DMSO-d$_6$) δ 7.81 (2H, dt, J=2.6, 8.8 Hz, 3,7-H), 8.55 (2H, dd, J=8.8, 2.6 Hz, 1,9-H), 8.78 (2H, dd, J=8.8, 4.8 Hz, 4,6-H); $^{13}$C NMR (100.6 MHz, DMSO-d$_6$) δ 113.5 (d, J=26.6 Hz), 119.7 (d, J=24.7 Hz), 123.3 (quartet, J=334.9 Hz), 124.9 (d, J=2.3 Hz), 132.4 (d, J=10.5 Hz), 114.7 (dd, J=11.1, 2.3 Hz), 166.6 (d, J=253.8 Hz). IR (KBr) 3010, 2985, 1590, 1581, 1475, 1434, 1220, 1206, 1179, 1124, 1113, 1079, 1042, 940, 912, 828, 749, 569, 491, 445, 410 cm-1; High resolution mass spectrum (ESI method) calcd for C$_{13}$H$_6$F$_5$S (M−Cl)$^+$, 289.0110. Found 289.0115. Elemental analysis: Calcd for C$_{13}$H$_6$F$_5$ClS: C, 48.09%; H, 1.86%. Found: C, 48.03%; H, 1.92%.

Example 9

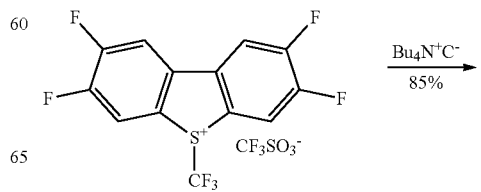

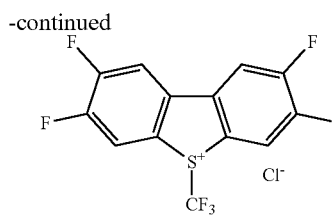

A solution of 1.68 g (6.0 mmol) of tetrabutylammonium chloride in 5 mL of acetonitrile was added to a stirred solution of 2.84 g (6.0 mmol) of 2,3,7,8-tetrafluoro-S-(trifluoromethyl)dibenzothiophenium trifluoromethanesulfonate in 80 mL of acetonitrile. After the mixture was stirred overnight, the resulting precipitates were collected by filtration to give 1.84 g (85%) of 2,3,7,8-tetrafluoro-S-(trifluoromethyl)dibenzothiophenium chloride as white solid. The pure sample was obtained by recrystallization from MeOH/tert-butyl methyl ether. The physical and spectral data are shown in the following: Decomposition-starting point 217° C. (by TGA/DSC): $^{19}$F NMR (376.5 MHz, DMSO-$d_6$) δ −51.84 (3F, S), −126.26 (2F, d, J=21.1 Hz), −130.44 (2F, d, J=21.5 Hz); $^1$H NMR (400.1 MHz, DMSO-$d_6$) δ 9.02 (2H, dd, J=9.2, 7.2 Hz), 8.76 (2H, dd, J=10.4, 7.2 Hz); $^{13}$C NMR (100.6 MHz, DMSO-d6) −114.91 (d, J=22.0 Hz, 1 or 4-C), −119.51 (d, J=24.2 Hz, 1 or 4-C), −123.13 (quartet, J=338.0 Hz, CF3SO3), −126.71 (d, J=7.6 Hz), −138.18 (d, J=10.2 Hz), −150.64 (dd, J=254.5, 14.2 Hz, 2 or 3-C), −154.35 (dd, J=256.2, 13.3 Hz, 2 or 3-C); IR (KBr) 3042, 29878, 1606, 1522, 1489, 1435, 1418, 1273, 1234, 1215, 1076, 999, 918, 895, 783, 750, 625, 571, 523, 455 cm$^{-1}$; High resolution mass spectrum (ESI method) calcd for [$C_{13}H_4F_7S$]$^+$ (M−Cl)$^+$ 324.9922. Found 324.9921. Elemental analysis: Calcd for $C_{13}H_4ClF_7S$: C, 43.29%; H, 1.12%. Found: C, 43.24%; H, 1.14%.

Example 10

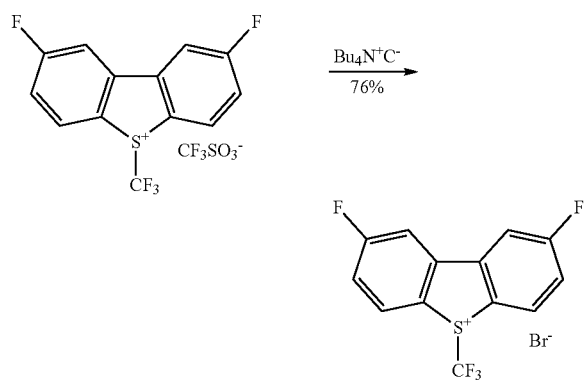

A round-bottomed flask was charged with 2.0 g (4.57 mmol) of 2,8-difluoro-S-(trifluoromethyl)dibenzothiophenium trifluoromethanesulfonate and 60 ml of acetonitrile. Into the homogeneous solution, was slowly added a solution of 1.47 g (4.57 mmol) of tetrabutylammonium bromide in 6 ml of acetonitrile. After stirring overnight, the resulting precipitates were filtered to obtain 1.28 g (76%) of 2,8-difluoro-S-(trifluoromethyl)dibenzothiophenium bromide as a yellow solid. The product was recrystallized from methanol, giving its methanol adduct as $C_{13}H_6BrS·½(CH_3OH)$. The physical and spectral data are as follows: Decomposition-starting point 182° C. (recrystallized from methanol) (by TGA/DSC); $^{19}$F NMR with $^1$H irradiation (376.5 MHz, DMS-$d_6$) δ −53.17 (3F, s, CF$_3$), −102.42 (2F, s, 2,8-F); $^1$H NMR (400.2 MHz, DMSO-$d_6$) δ 8.82 (2H, dd, J=4.6, 8.8 Hz, 4,6-H), 8.57 (2H, dd, J=2.8, 8.8 Hz, 1,9-H), 7.81 (2H, dt, J=2.8, 8.8 Hz, 3,7-H), 4.0 (broad peak, OH), 3.17 (1.4H, s, CH$_3$); $^{13}$C NMR (100.6 MHz, DMSO-$d_6$) δ 166.7 (d, J=254.5 Hz), 143.7 (dd, J=2.0, 11.1 Hz), 132.6 (d, J=10.1 Hz), 127.6 (s), 122.6 (quartet, J=334.3 Hz), 119.9 (d, J=24.1 Hz), 113.6 (d, J=27.2 Hz), 48.9 (s); IR (KBr) 3443, 3019, 2990, 1583, 1475, 1438, 1300, 1217, 1178, 1124, 1081, 1041, 945, 902, 829, 750, 721, 568, 491, 441, 411 cm$^{-1}$; High resolution mass spectrum (ESI method) calcd for $C_{13}H_6F_5S$ (M−Br)$^+$, 289.0110. Found 289.0113. Elemental analysis: Calcd for $C_{13}H_6BrF_5S·½CH_3OH$: C, 42.10%; H, 2.09%. Found: C, 41.90%; H, 1.94%.

Example 11

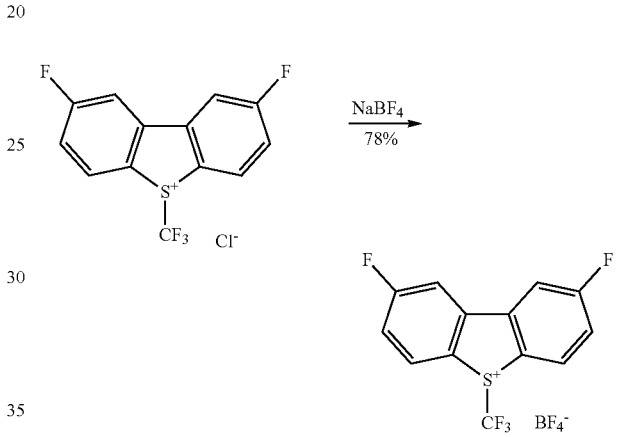

2,8-Difluoro-S-(trifluoromethyl)dibenzothiophenium chloride (0.30 g, 0.924 mmol) was added into a stirred solution of sodium tetrafluoroborate (0.101 g, 0.920 mmol) in methanol (5 mL) at 40° C. After the mixture became a homogeneous solution, it was cooled to room temperature and then 15 mL of acetonitrile was added slowly. The resulting white precipitate (NaCl) was removed by filtration, and the filtrate was evaporated up. After acetonitrile (15 mL) was added, the insoluble solid was removed by filtration and the filtrate was evaporated up to give the product as a crystalline solid, which was recrystallized from acetonitrile-diethyl ether, giving 0.27 g (78% yield) of pure 2,8-difluoro-S-(trifluoromethyl)dibenzothiophenium tetrafluoroborate. The properties and spectral data are shown in the following: decomposition-starting point 185° C. (by TGA/DSC) (recrystallized from acetonitrile-diethyl ether); $^{19}$F NMR with $^1$H irradiation (376.5 MHz, DMSO-$d_6$) δ −53.24 (3F, s, CF$_3$), −101.80 (2F, s, 2,8-F), −148.24 (4F, s, BF$_4$); $^1$H NMR (400.2 MHz, DMSO-$d_6$) δ 7.82 (2H, dt, J=2.6, 8.9 Hz, 3,7-H), 8.55 (2H, J=8.8, 2.6 Hz, 1,9-H), 8.75 (2H, J=8.8, 4.8 Hz, 4,6-H); $^{13}$C NMR (100.6 MHz, DMSO-$d_6$) δ 113.7 (d, J=26.6 Hz), 120.1 (d, J=24.6 Hz), 123.0 (quartet, J=332.2 Hz), 132.9 (d, J=10.7 Hz), 143.8 (dd, J=11.0, 2.3 Hz), 116.9 (d, J=254.7 Hz); IR (KBr) 3101, 2984, 1591, 1479, 1437, 1300, 1252, 1223, 1182, 1082, 943, 881, 829, 756, 573, 522, 490, 456, 441, 429, 409 cm$^{-1}$; High resolution mass spectrum (ESI method) calcd for $C_{13}H_6F_5S$ (M−BF$_4$)$^+$, 289.0110. Found 289.0110. Elemental analysis: Calcd for $C_{13}H_6F_9SB$: C, 41.52%; H, 1.61%. Found: C, 41.78%; H, 1.64%.

Example 12

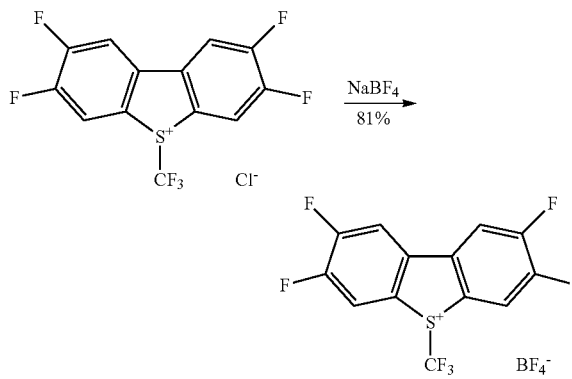

Sodium tetrafluoroborate (0.33 g, 3 mmol) was added to a stirred solution of 2,3,7,8-tetrafluoro-S-(trifluoromethyl)dibenzothiophenium chloride (1.08 g, 3 mmol) in methanol (15 mL). The mixture was stirred at room temperature for 1 hr and then 30 mL of acetonitrile was added dropwise. The resulting precipitate (NaCl) was removed by filtration and the filtrate was evaporated up to dryness. After acetonitrile (30 mL) was added, the insoluble solid (NaCl) was removed by filtration and the filtrate was evaporated up to dryness, giving 0.99 g (80% yield) of the product as white solid. The pure product was obtained by recrystallization from acetonitrile/tert-butyl methyl ether. The physical and spectral data are shown in the following: Decomposition-starting point 152° C. (by TGA/DSC): $^{19}$F NMR (376.5 MHz, DMSO-$d_6$) δ −51.50 (3F, s), −124.92 (2F, d, J=21.5 Hz), −129.45 (2F, d, J=21.5 Hz), −148.21 (4F, s); $^1$H NMR (400.1 MHz, DMSO-$d_6$) δ 8.86 (2H, dd, J=8.6, 7.4 Hz), 8.75 (2H, dd, J=10.0, 7.2 Hz); $^{13}$C NMR (100.6 MHz, DMSO-$d_6$) δ −115.18 (d, J=22.1 Hz, 1 or 4-C), −120.02 (d, J=24.1 Hz, 1 or 4-C), −123.19 (quartet, J=333.7 Hz, CF$_3$SO$_3$), −123.66 (d, J=7.6 Hz), −138.38 (d, J=10.5 Hz), −150.96 (dd, J=255.6, 14.2 Hz, 2 or 3-C), −154.92 (dd, J=257.3, 13.1 Hz, 2 or 3-C); IR (KBr) 3063, 1609, 1489, 1437, 1420, 1279, 1246, 1179, 1040, 1001, 899, 783, 756, 625, 571, 523, 457 cm$^{-1}$; High resolution mass spectrum (ESI method) calcd for [C$_{13}$H$_4$F$_7$S]$^+$ (M−BF$_4$)$^+$ 324.9922. Found 324.9925.

Example 13

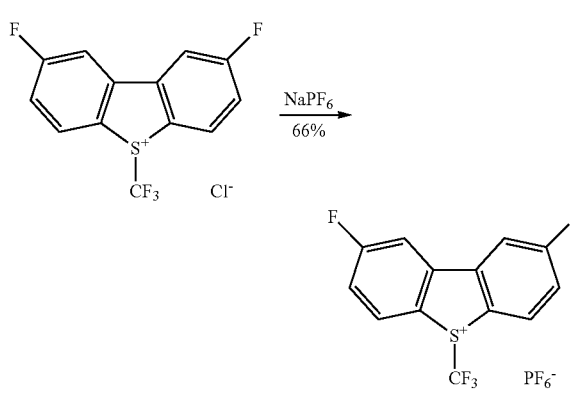

A round-bottomed flask was charged with 1.09 g (6.47 mmol) of sodium hexafluorophosphate and 20 ml of methanol. After the mixture became homogeneous, 2.1 g (6.47 mmol) of 2,8-difluoro-S-(trifluoromethyl)dibenzothiophenium chloride was added and the mixture was stirred for 1 hr. Into the homogeneous solution, 150 mL of acetonitrile was added and the mixture was stirred for 2 hrs. The resulting precipitate (NaCl) was removed by filtration and the filtrate was evaporated to dryness. Into the residue, 120 mL of acetonitrile was added and the resulting precipitates (NaCl) was removed by filtration. The filtrate was evaporated to dryness to give the crystalline solid, which was recrystallized from acetonitrile-diethyl ether to give 1.84 g (66%) of 2,8-difluoro-S-(trifluoromethyl)dibenzothiophenium hexafluorophosphate as white crystals. Decomposition-starting point 186° C. (by TGA/DSC); $^{19}$F NMR with $^1$H-irradiation (376.5 MHz, DMSO-$d_6$) δ −53.23 (3F, s, CF$_3$), −70.13 (6F, d, J=711.2 Hz, PF$_6$), −101.80 (2F, s, 2,8-F); $^1$H NMR (400.2 MHz, DMSO-$d_6$) δ 8.76 (2H, dd, J=4.6, 8.9 Hz, 4,6-H), 8.56 (2H, dd, J=2.7, 8.9 Hz, 1,9-H), 7.83 (2H, dt, J=2.7, 8.9 Hz, 3,7-H); $^{13}$C NMR (100.6 MHz, DMSO-$d_6$) δ −166.9 (d, J=254.7 Hz, 2,8-C), −143.7 (dd, J=11.1, 2.0 Hz, 10,11-C), −132.9 (d, J=10.6 Hz, 4,6-C), −123.4 (quartet, J=331.4 Hz, CF$_3$), −123.0 (d, J=2.2 Hz, 12,13-C), −120.1 (d, J=24.6 Hz, 1,9- or 3,8-C), −113.7 (d, J=26.2 Hz, 1,9- or 3,8-C); IR (KBr) 3101, 1596, 1481, 1440, 1413, 1302, 1260, 1233, 1178, 1128, 1067, 1043, 944, 894, 845, 822, 756, 742, 571, 558, 491, 454, 431, 409 cm$^{-1}$; High resolution mass spectrum (ESI method) calcd for C$_{13}$H$_6$F$_5$S (M−PF$_6$)$^+$, 289.0110. Found 289.0106.

Example 14

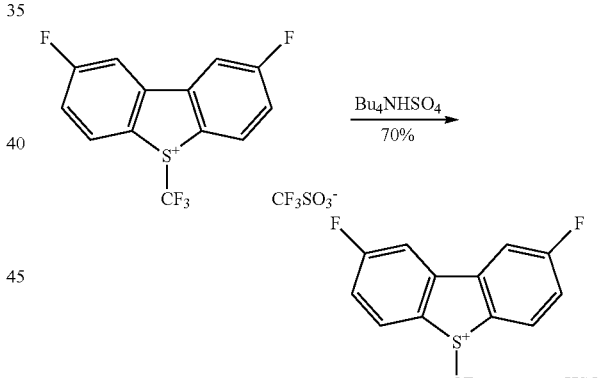

A solution of 1.09 g (3.20 mmol) of tetrabutylammonium sulfate in 6 mL of acetonitrile was dropwise added to a stirred solution of 1.49 g (3.20 mmol) of 2,8-difluoro-S-(trifluoromethyl)dibenzothiophenium trifluoromethanesulfonate in 25 mL of acetonitrile at room temperature. The mixture was then stirred overnight at room temperature. After that, the reaction mixture was filtered to give 0.89 g (70%) of 2,8-difluoro-S-(trifluoromethyl)dibenzothiophenium sulfate as white solid. The solid was recrystallized from methanol-diethyl ether to get a sample for analysis. The crystals obtained by the recrystallization were assigned as monohydrate by the elemental analysis below. Decomposition-starting point 155° C. (by TGA/DSC); $^{19}$F NMR with $^1$H-irradiation (376.5 MHz, DMSO-d$_6$) δ –53.27 (3F, s, CF$_3$), –101.81 (2F, s, 2,8-F); $^1$H NMR (400.2 MHz, DMSO-d$_6$) δ 8.76 (2H, dd, J=4.8, 9.0 Hz, 4,6-H), 8.56 (2H, dd, J=2.4, 9.0 Hz, 1,9-H), 7.83 (2H, dt, J=2.4, 8.8 Hz, 3, 7-H); $^{13}$C NMR (100.6 MHz, DMSO-d$_6$) δ –166.9 (d, J=254.7 Hz, 2,8-C), –143.8 (dd, J=11.2, 2.3 Hz, 10,11-C), –132.9 (d, J=10.6 Hz, 4,6-C), –123.4 (quartet, J=332.0 Hz, CF$_3$), –123.0 (d, J=2.4 Hz, 12,13-C), –120.1 (d, J=24.7 Hz, 1,9- or 3,8-C), –113.7 (d, J=26.6 Hz, 1,9- or 3,8-C); IR (KBr) 2983, 1592, 1581, 1507, 1477, 1436, 1213, 1177, 1123, 1082, 1040, 943, 884, 827, 584, 567, 490, 441 cm$^{-1}$. High resolution mass spectrum (ESI method): Calcd for [C$_{13}$H$_6$F$_5$S]$^+$ (M–HSO$_4$)$^+$ 289.0110. Found 289.0109. Elemental analysis: Calcd for C$_{13}$H$_7$F$_5$O$_4$S$_2$·H$_2$O: C, 38.62%; H, 2.24%. Found: C, 38.79%; H, 2.53%.

Example 15

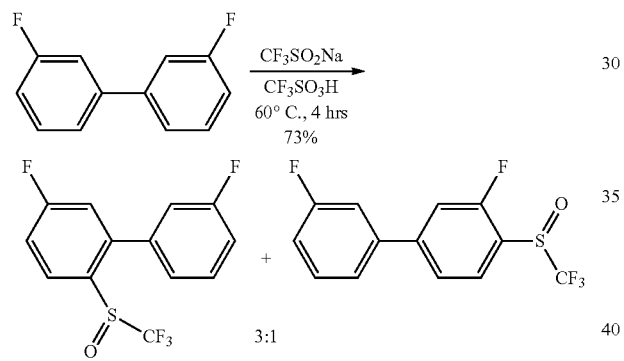

Under an atmosphere of nitrogen, 100 mL three-necked round bottom flask was charged with sodium trifluoromethanesulfinate (3.9 g, 25 mmol) and trifluoromethanesulfonic acid (13.2 mL, 0.15 mol). After stirring for 5 min, 3,3'-difluorobiphenyl (4.75 g, 25 mmol) was added, and the reaction mixture was heated to 60° C. After stirring for 4 hrs at 60° C., the reaction mixture was mixed with 20 mL of water, neutralized by 35 mL of saturated aqueous sodium carbonate solution, and extracted with ethyl acetate. The organic layer was dried with magnesium sulfate and filtered. The filtrate was evaporated up to dryness and the resulting residue was purified by column chromatography on silica gel to give 5.59 g (73%) of a yellow oil, which was a 3:1 mixture of 3,3'-difluoro-6-(trifluoromethylsulfinyl)biphenyl and 3,3'-difluoro-4-(trifluoromethylsulfinyl)biphenyl. These isomers were isolated in pure form by careful column chromatography on silica gel and identified. Each of these isomer's physical and spectral data are shown in the following: 3,3'-Difluoro-6-(trifluoromethylsulfinyl)biphenyl: oil; $^{19}$F NMR with $^1$H-irradiation (376.5 MHz, DMSO-d$_6$) δ –73.05 (3F, s, CF$_3$), –105.75 (1F, s, 3 or 3'-F), –112.29 (1F, 3 or 3'-F); $^1$H NMR (400.1 MHz, DMSO-d$_6$) δ 7.33 (1H, br. dt, J=1.7, 8.6 Hz, 5-H), 7.43-7.62 (4H, m), 7.69 (1H, dt, J=2.5, 8.4 Hz), 8.16 (1H, dd, J=5.6, 8.8 Hz); $^{13}$C NMR (100.6 MHz, DMSO-d$_6$) δ 116.3 (d, J=21.0 Hz), 116.8 (d, J=19.8 Hz), 117.0 (d, J=19.6 Hz), 119.1 (d, J=23.4 Hz), 125.5 (quartet, J=340.2 Hz, CF$_3$), 126.1 (d, J=2.6 Hz), 129.0 (d, J=10.3 Hz), 130.1 (s, 6-C), 131.3 (d, J=8.5 Hz), 138.1 (d, J=8.0 Hz), 143.7 (d, J=8.6 Hz), 162.4 (d, J=244.8 Hz, 3 or 3'-C), 165.3 (d, J=252.9 Hz, 3 or 3'-C); IR (nujol) 2959, 2926, 2857, 1578, 1468, 1138, 1090, 872, 829, 789 cm$^{-1}$. High resolution mass spectrum (ESI method) calcd for C$_{13}$H$_7$F$_5$OS 307.0211 (M+H)$^+$. Found (M+H)$^+$ 307.0225. Another isomer, 3,3'-difluoro-4-(trifluoromethylsulfinyl)biphenyl: oil; $^{19}$F NMR with $^1$H-irradiation (376.6 MHz, CDCl$_3$) δ –74.02 (3F, d, J=10 Hz, CF$_3$), –111.76 (1F, s, 3'-F), –112.23 (1F, quartet, J=10 Hz, 3-F); $^1$H NMR (400.1 MHz, CDCl$_3$) δ 7.16 (1H, td, J=8.4, 2.0 Hz), 7.31 (1H, dm, J=10.0 Hz), 7.37-7.53 (3H, m), 7.65 (1H, dd, J=8.6, 1.4 Hz), 8.04 (1H, t, J=7.4 Hz, 4-H). High resolution mass spectrum (ESI method) calcd for C$_{13}$H$_7$F$_5$OS 307.0211 (M+H)$^+$. Found (M+H)$^+$ 307.0208.

Example 16

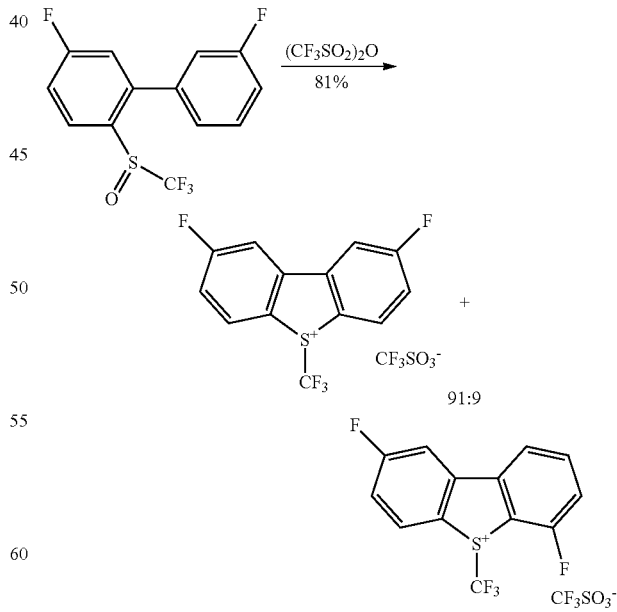

A starting material, 3,3'-difluoro-6-(trifluoromethylsulfinyl)biphenyl (2.98 g, 9.72 mmol), was used as a 3.5:1 mixture of 3,3'-difluoro-6-(trifluoromethylsulfinyl)biphenyl and 3,3'-difluoro-4-(trifluoromethylsulfinyl)biphenyl. The starting material was dissolved in 12.5 mL of dry nitromethane and the mixture was cooled to 0-5° C. on an ice bath. Into the cooled solution was dropwise added 3.53 g (12.5 mmol) of trifluoromethanesulfonic anhydride. After stirring at room temperature overnight, the reaction mixture was evaporated to dryness under reduce pressure. The residue was mixed with 10 mL of toluene and 10 mL of water and the mixture was stirred for 30 min. The resulting precipitates were collected by filtration and washed with 10 mL of toluene and then with 20 mL of ethyl acetate, giving 3.45 g (81%) of a 91:9 mixture of 2,8-difluoro-S-(trifluoromethyl)dibenzothiophenium trifluoromethanesulfonate and 2,6-difluoro-S-(trifluoromethyl)dibenzothiophenium trifluoromethanesulfonate as white crystals. These products were identified by the spectral analysis. The data are shown in Example 1.

analysis; $^{19}$F NMR (376.5 MHz, CDCl$_3$) δ −69.3 (s, CF$_3$). The $^{19}$F NMR analysis showed that 2,8-difluorodibenzothiophene and 2,6-difluorodibenzothiophene were produced in 91% and 3% yield, respectively, based on the difluoro-S-(trifluoromethyl)dibenzothiophenium trifluoromethanesulfonates used. Their spectral data are shown in the following. 2,8-Difluorodibenzothiophene: $^{19}$F NMR with $^1$H irradiation (376.5 MHz, CDCl$_3$) δ −117.81 (s); $^1$H NMR (400.2 MHz, CDCl$_3$) δ 7.24 (2H, dt, J=2.4, 8.8 Hz, 3,7-H), 7.75 (2H, dd, J=2.4, 9.2 Hz, 1,9-H), 7.78 (2H, dd, J=4.8, 8.8 Hz, 4,6-H). 2,6-Difluorodibenzothiophene: $^{19}$F NMR with $^1$H irradiation (376.5 MHz, DMSO-d$_6$) δ −115.33 (s, 6-F), −117.32 (s, 2-F).

Examples 18, 19, and 20

2,8-Difluoro-S-(trifluoromethyl)dibenzothiophenium salt (0.75 mmol) was added to a stirred solution of methyl 1-oxo-2-indanecarboxylate (0.5 mmol), K$_2$CO$_3$ (1.5 mmol), Example 17

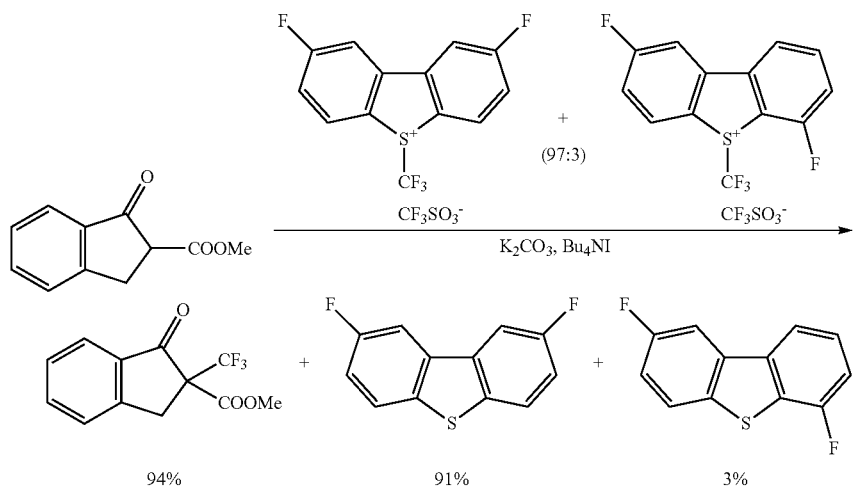

To a stirred solution of methyl 1-oxo-2-indanecarboxylate (190 mg, 1 mmol), K$_2$CO$_3$ (430 mg, 3 mmol), and tetrabutylammonium iodide (20 mg, 0.05 mmol) in N,N-dimethylformamide (DMF) (10 mL), was added a 97:3 mixture of 2,8-difluoro-S-(trifluoromethyl)dibenzothiophenium trifluoromethanesulfonate and 2,6-difluoro-S-(trifluoromethyl)dibenzothiophenium trifluoromethanesulfonate (650 mg, 1.5 mmol) at room temperature. The mixture was stirred for 3 hrs. The trifluoromethylated product, methyl 1-oxo-2-(trifluoromethyl)indane-2-carboxylate, was found to be produced in 94% yield by $^{19}$F NMR analysis of the reaction solution using benzotrifluoride as a standard. The product was isolated by the standard post-treatment (extraction and column chromatography) and identified by the spectral and tetrabutylammonium iodide (0.025 mmol) in 5 mL of N,N-dimethylformamide (DMF) at room temperature under nitrogen atmosphere. The mixture was stirred for 1 h. The reaction mixture was analyzed by $^{19}$F NMR using 4-chlorobenzotrifluoride as a standard. As 2,8-difluoro-S-(trifluoromethyl)dibenzothiophenium salt, 2,8-difluoro-S-(trifluoromethyl)dibenzothiophenium trifluoromethanesulfonate (Example 18), 2,8-difluoro-S-(trifluoromethyl)dibenzothiophenium chloride (Example 19), and 2,8-difluoro-5-(trifluoromethyl)dibenzothiophenium tetrafluoroborate (Example 20) were used. The $^{19}$F NMR analysis showed that the trifluoromethylated product, methyl 1-oxo-2-(trifluoromethyl)indane-2-carboxylate, was produced in 85%, 91%, and 100% yield in Examples 18, 19, and 20, respectively (See Table 2). The CF$_3$-product was isolated by the standard post-treatment and identified by spectral analysis: $^{19}$F NMR (376.5 MHz, CDCl$_3$) δ −69.3 (s, CF$_3$).

TABLE 2

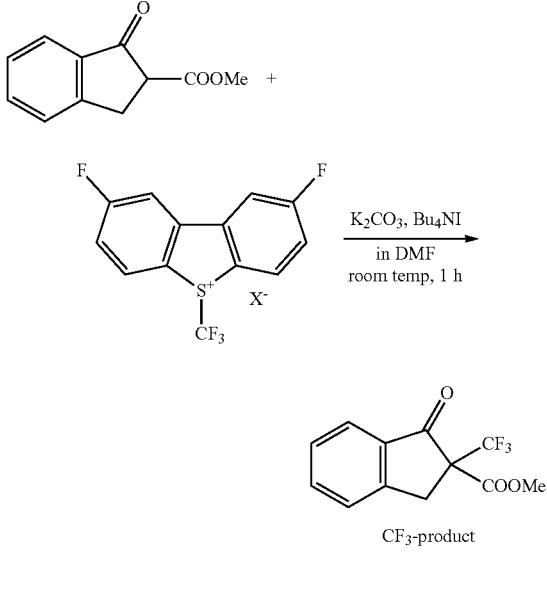

| Example | 2,8-Difluoro-S—CF$_3$-dibenzothiophenium salt | Yield of CF$_3$-product |
|---|---|---|
| Example 18 | X = TfO | 85% |
| Example 19 | X = Cl | 91% |
| Example 20 | X = BF$_4$ | 100% |

Example 21

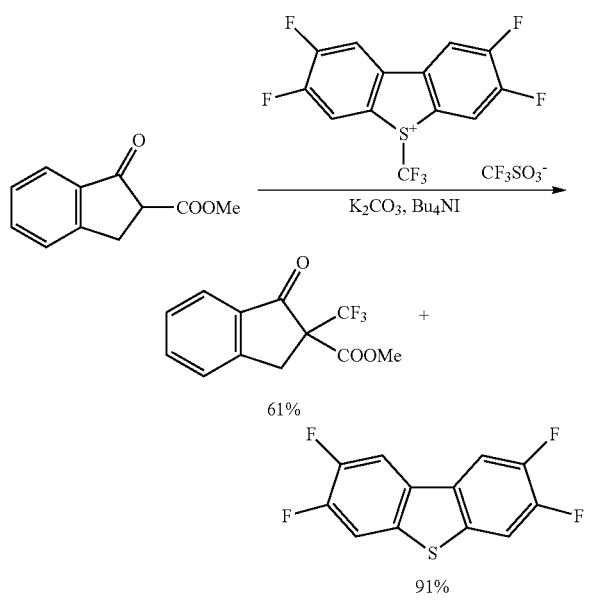

To a stirred solution of methyl 1-oxo-2-indane-carboxylate (114 mg, 0.6 mmol), K$_2$CO$_3$ (249 mg, 1.8 mmol), and tetrabutylammonium iodide (10 mg, 0.03 mmol) in N,N-dimethylformamide (3 mL), was added 2,3,7,8-tetrafluoro-S-(trifluoromethyl)dibenzothiophenium trifluoromethanesulfonate (430 mg, 0.9 mmol) at room temperature. The mixture was stirred for 4 hrs. $^{19}$F NMR analysis of the reaction solution using benzotrifluoride as a standard showed that methyl 1-oxo-2-(trifluoromethyl)indane-2-carboxylate was produced in 61% yield based on the amount of methyl 1-oxo-2-indanecarboxylate used and 2,3,7,8-tetrafluorodibenzothiophene was produced in 91% yield based on the amount of 2,3,7,8-tetrafluoro-S-(trifluoromethyl)dibenzothiophenium trifluoromethanesulfonate used. After that, the reaction solution was diluted with water (30 mL) and extracted with ethyl acetate (3×30 mL), and then the combined organic layers were dried over MgSO$_4$, filtered, and evaporated up. The resulting residue was column chromatographed on silica gel. The products were isolated and identified by the spectral analysis. The data of methyl 1-oxo-2-(trifluoromethyl)indane-2-carboxylate was shown in Example 17. The physical and spectral data of 2,3,7,8-tetrafluorodibenzothiophene are shown in the following: 2,3,7,8-Tetrefluorodibenzophenone: mp 145.3-147.3° C.; $^{19}$F NMR with $^1$H irradiation (376.5 MHz, CDCl$_3$) δ −136.41 (2F, d, J=20.7 Hz, 3,7- or 2,8-F), −139.69 (2F, d, J=20.7 Hz, 2,8- or 3,7-F); $^1$H NMR (400.2 MHz, CDCl$_3$) δ 7.61 (2H, dd, J=9.6, 6.8 Hz, 4,6- or 1,9-H), 7.77 (2H, dd, J=10.0, 7.2 Hz, 1,9- or 4,6-H); $^{13}$C NMR (100.6 MHz, CDCl$_3$) δ 109.4 (d, J=19.4 Hz), 111.0 (d, J=21.2 Hz), 130.7 (m), 135.1 (d, J=7.8 Hz), 149.4 (dd, J=247.0, 14.2 Hz), 150.1 (dd, J=250.7, 14.7 Hz); IR (KBr) 3076, 1577, 1490, 1439, 1263, 1151, 1059, 907, 861, 831, 774, 666, 625, 572, 520, 438 cm$^{-1}$.

Examples 22, 23, and 24

A mixture of a halogenated S-(trifluoromethyl)dibenzothiophenium salt (1 mmol), aniline (2 mmol), and 4-chlorobenzotrifluoride (1 mmol) in N,N-dimethylformamide (DMF) (2 mL) was stirred at 30° C. for 3 hrs under nitrogen atmosphere. As a halogenated S-(trifluoromethyl)dibenzothiophenium salt, 2,3,7,8-tetrafluoro-S-(trifluoromethyl)dibenzothiophenium trifluoromethanesulfonate (Example 22), 2,8-difluoro-S-(trifluoromethyl)dibenzothiophenium trifluoromethanesulfonate (Example 23), and 2,6-difluoro-S-(trifluoromethyl)dibenzothiophenium trifluoromethanesulfonate (Example 24) were used. A half (1 mmol) of aniline (2 mmol) was used as a base for the reaction because this reaction generated 1 mmol of trifluoromethanesulfonic acid. 4-Chlorobenzotrifluoride was a standard for $^{19}$F NMR analysis. Each of the reaction mixtures was analyzed by $^{19}$F NMR. The results are shown in Table 3. The products, 2- and 4-(trifluoromethyl)aniline, were identified by spectral comparison with authentic samples.

The comparison among Examples 22, 23, and 23 showed that the reactivity increased in the order of 2,8-difluoro-S-(trifluoromethyl)dibenzothiophenium salt <2,6-difluoro-S-(trifluoromethyl)dibenzothiophenium salt <2,3,7,8-tetrafluoro-S-(trifluoromethyl)dibenzothiophenium salt. In particular, the 2,3,7,8-tetrafluoro-S-(trifluoromethyl)dibenzothiophenium salt provided trifluoromethylated anilines in good yields for short reaction time.

TABLE 3

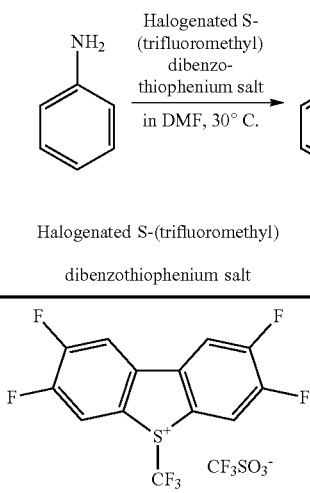

| Example | Halogenated S-(trifluoromethyl) dibenzothiophenium salt | Reaction time | Reaction conversion | Yield 2-CF$_3$-aniline | Yield 4-CF$_3$-aniline |
|---|---|---|---|---|---|
| Example 22 | 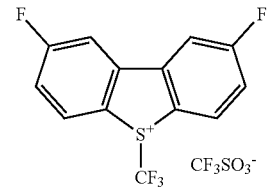 | 3 h | 78% | 44% (56%*) | 23% (29%*) |
| Example 23 | 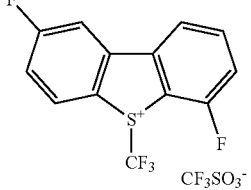 | 3 h | 30% | 14% | 6% |
| Example 24 | 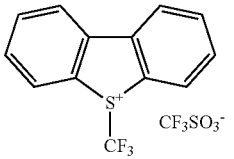 | 3 h | 64% | 37% | 17% |
| Comparison Example 2 | Umemoto reagent | 3 h | 7% | 5% | 2% |

*These yields were calculated based on the consumed aniline.

Comparison Example 2

The reaction of aniline with S-(trifluoromethyl)dibenzothiophenium trifluoromethanesulfonate (Umemoto reagent) was carried out in the same manner as for Examples 22-24 except that Umemoto reagent was used in place of a halogenated S-(trifluoromethyl)dibenzothiophenium salt. The results are shown in Table 3.

The comparison of Comparison Example 2 with Examples 22, 23, and 24 showed that the halogenated S-(perfluoroalkyl)dibenzothiophenium salts are more powerful than Umemoto reagent.

Example 25

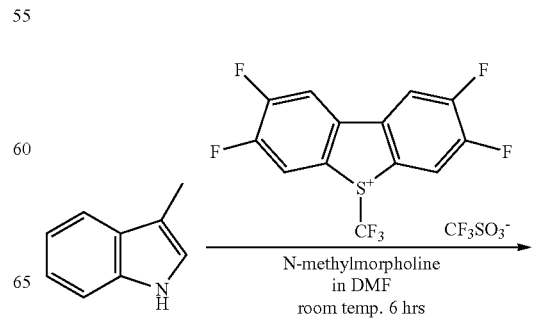

-continued

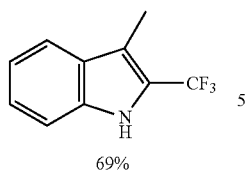

69%

2,3,7,8-Tetrafluoro-S-(trifluoromethyl)dibenzothiophenium trifluoromethanesulfonate (0.6 mmol) was added to a stirred solution of 3-methylindole (0.5 mmol) and N-methylmorpholine (0.75 mmol) in N,N-dimethylformamide (DMF) (2 mL) under nitrogen atmosphere and the reaction mixture was stirred for 6 hrs at room temperature. The reaction mixture was analyzed by $^{19}$F NMR using 4-chlorobenzotrifluoride as a standard. The analysis showed that 2-trifluoromethyl-3-methylindole was produced in 69% yield. The product was isolated by the standard post-treatment including column chromatography on silica gel and identified by the spectral analysis: $^{19}$F NMR (376.6 MHz, CDCl$_3$) δ −58.64 ppm (s, CF$_3$).

Example 26

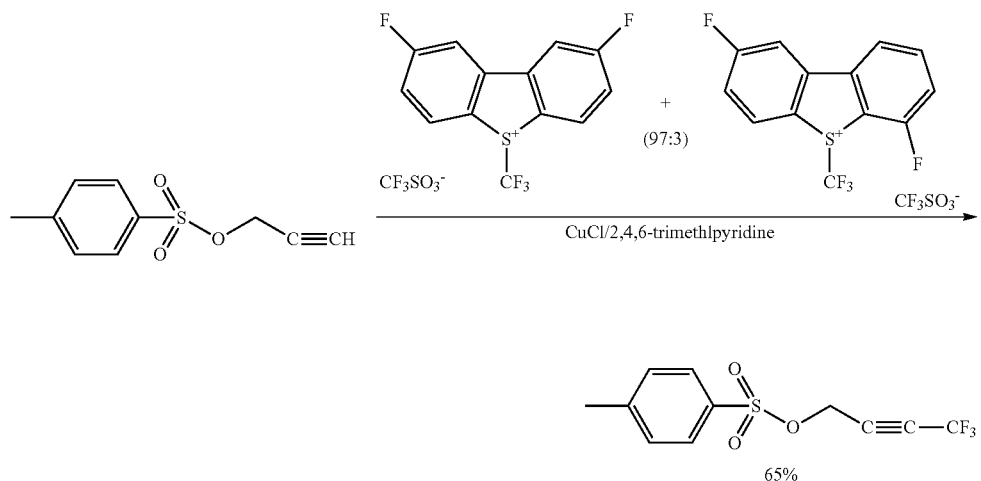

CuCl (0.2 mmol), 2,4,6-trimethylpyridine (2 mmol), a 97:3 mixture of 2.8-difluoro-S-(trifluoromethyl)dibenzothiophenium trifluoromethanesulfonate and 2,6-difluoro-S-(trifluoromethyl)dibenzothiophenium trifluoromethanesulfonate (525 mg, 1.2 mmol), and 4-(p-toluenesulfonyloxy)-1-butyne (1 mmol) were added to a Schlenk tube which was equipped with a stirring bar. N,N-Dimethylacetamide (5 mL) was added to the tube under argon atmosphere and then the reaction mixture was stirred for 24 hrs at 30° C. The trifluoromethylated product, 5-phenylsulfonyloxy-1,1,1-trifluoro-2-pentyne, was found to be produced in 65% yield by $^{19}$F NMR analysis of the reaction solution using benzotrifluoride as a standard. The product was isolated by the standard post-treatment (extraction and column chromatography) and identified by comparison with the reported spectral data of the product; $^{19}$F NMR with $^1$H irradiation (376.5 MHz, CDCl$_3$) δ −50.31 (s, CF$_3$).

Example 27

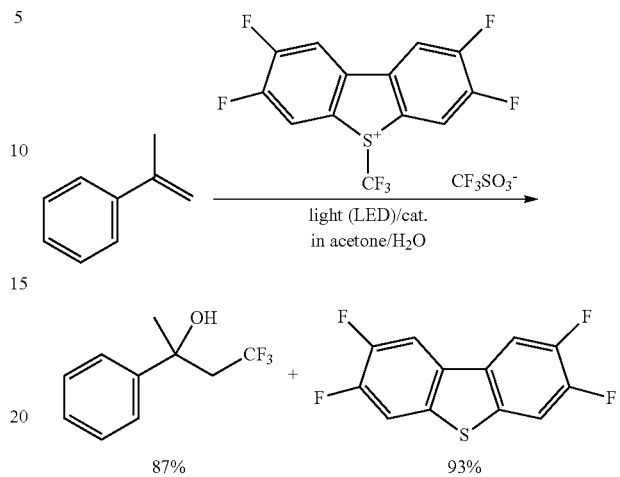

A 100 mL-Schlenk tube was charged with ∂-methylstyrene (236 mg, 2.0 mmol), 2,3,7,8-tetrafluoro-S-(trifluoromethyl)dibenzothiophenium trifluoromethanesulfonate (1.04 g, 2.2 mmol), tris(2,2'-bipyridine)ruthenium(II) hexafluorophosphate (9 mg, 0.01 mmol), and acetone (16 mL), and water (2 mL) under nitrogen atmosphere. The tube was placed at a distance of less than 1 cm from 4 W LED lamp. The solution was irradiated at room temperature for 4.5 hrs. $^{19}$F NMR of the reaction solution using benzotrifluoride as a standard showed that 3,3,3-trifluoro-1-methyl-1-phenyl-1-propanol was produced in 87% yield based on α-methylstyrene used and 2,3,7,8-tetrafluorodibenzothiophene was produced in 93% yield based on the 2,3,7,8-tetrafluoro-S-(trifluoromethyl)dibenzothiophenium trifluoromethanesulfonate used. The trifluoromethyl product was isolated by the standard post-treatment (extraction and column chromatography) and identified by spectral analysis; $^{19}$F NMR with $^1$H irradiation (376.5 MHz, CDCl$_3$) δ −60.07 (s, CF$_3$).

Example 28

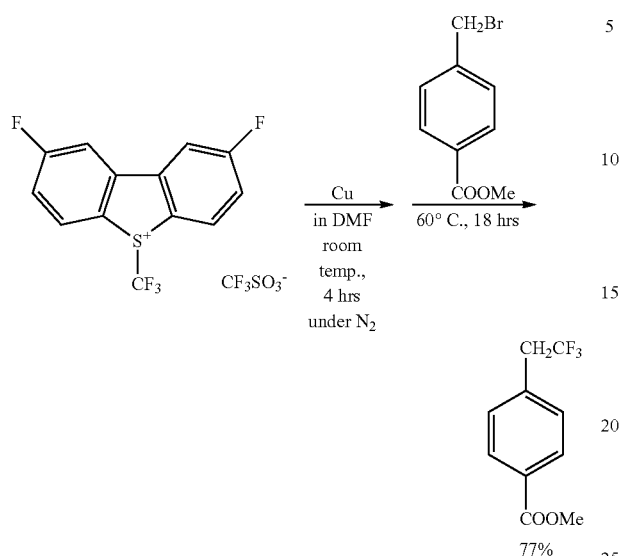

A mixture of 2,8-difluoro-S-(trifluoromethyl)dibenzothiophenium trifluoromethanesulfonate (10 mmol) and copper powder (15 mmol) in dry N,N-dimethylformamide (DMF) was stirred for 4 hrs at room temperature under nitrogen atmosphere. Methyl 4-(bromomethyl)benzoate (5 mmol) was added to the mixture and the reaction mixture was stirred at 60° C. overnight (18 hrs). $^{19}$F NMR analysis of the reaction mixture using benzotrifluoride as a standard showed that methyl 4-(2',2',2'-trifluoroethyl)benzoate was produced in 77% yield. The product was isolated by the standard post-treatment and identified by spectral analysis; $^{19}$F NMR with $^1$H irradiation (376.5 MHz, CDCl$_3$) δ −65.57 (s, CF$_3$).

Example 29

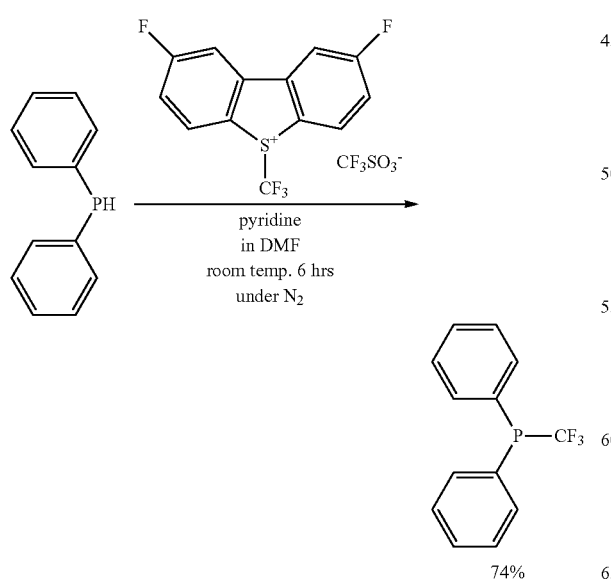

To a stirred solution of diphenylphosphine (0.5 mmol) and pyridine (0.6 mmol) in N,N-dimethylformamide (DMF), was added 2,8-difluoro-S-(trifluoromethyl)dibenzothiophenium trifluoromethanesulfonate (0.6 mmol) at room temperature under nitrogen atmosphere. The reaction mixture was stirred at room temperature for 6 hrs. $^{19}$F NMR analysis of the reaction mixture using 4-chlorobenzotrifluoride as a reference showed that (trifluoromethyl)diphenhylphophine was produced in 74% yield. The product was isolated by post-treatment and identified by spectral analysis: $^{19}$F NMR (376.6 MHz, CDCl$_3$) δ −55.14 (d, J=73.1 Hz).

Example 30

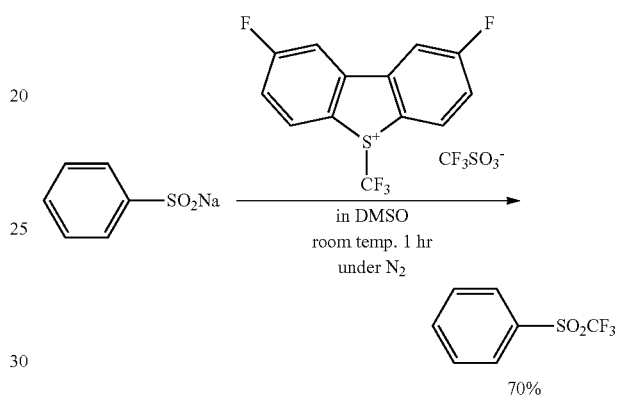

2,8-Difluoro-S-(trifluoromethyl)dibenzothiophenium trifluoromethanesulfonate (1.0 mmol) was added to a stirred solution of sodium benzenesulfinate (1.0 mmol) and 4-chlorobenzotrifluoride (1.0 mmol) in 5 mL of dimethylsulfoxide (DMSO) at room temperature under nitrogen atmosphere and the mixture was stirred for 1 h. 4-Chlorobenzotrifluoride was a reference for $^{19}$F NMR analysis. The $^{19}$F NMR analysis of the reaction mixture showed that phenyl trifluoromethyl sulfone was produced in 70% yield. The product was isolated by the standard post-treatment and identified by spectral analysis: $^{19}$F NMR (376.6 MHz, CDCl$_3$) δ −78.50 ppm (s, CF$_3$).

Example 31

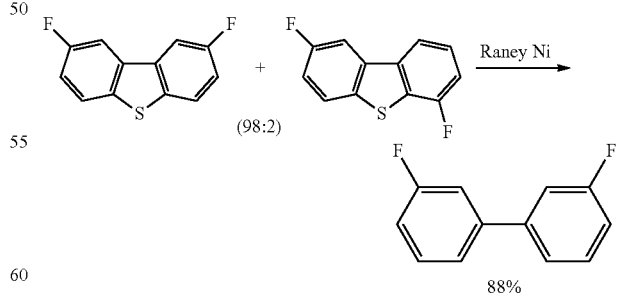

A 98:2 mixture (0.10 g, 0.45 mmol) of 2,8- and 2,6-difluorodibenzothiophene, 0.8 mL (in ethanol) of Raney Ni (sponge nickel catalysis A-4F00 from Johnson Matthey, USA), and 20 mL of ethanol were mixed, and the mixture was heated under reflux for 4 hrs. After that, $^{19}$F NMR analysis of the reaction solution using fluorobenzene as a standard showed that 3,3'-difluorobiphenyl was produced in 88% yield. The product was isolated by the standard post-treatment and identified by spectral comparison with an authentic sample.

Example 32

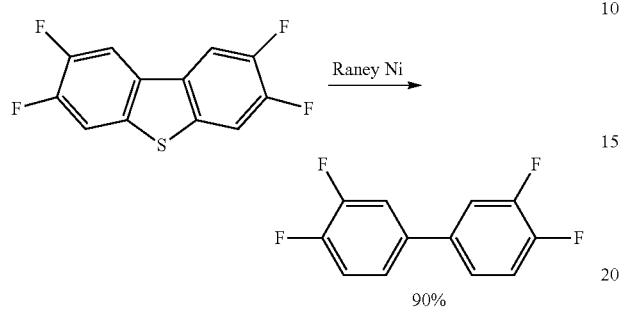

90%

2,3,7,8-Tetrafluorodibenzothiophene (128 mg, 0.5 mmol), 1.2 mL (in ethanol) of Raney Ni (A-7F63 from Johnson Matthey, USA), and 20 mL of ethanol were mixed, and the mixture was heated under reflux for 4 hrs. After that, $^{19}$F NMR analysis of the reaction solution using 4-chlorobenzotrifluoride as a standard showed that 3,3',4,4'-tetrafluorobiphenyl was produced in 90% yield. The product was isolated by the standard post-treatment and identified by spectral comparison with an authentic sample.

We claim:

1. Fluorinated S-(perfluoroalkyl)dibenzothiophenium salt represented by the following general formula (I):

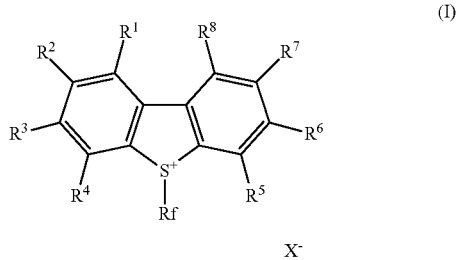

(I)

X⁻ wherein Rf is a perfluoroalkyl group having 1 to 4 carbons; $R^1$, $R^2$, $R^3$, $R^4$, $R^5$, $R^6$, $R^7$ and $R^8$ each is a hydrogen atom or a fluorine atom, provided that the total number of fluorine atoms of $R^{1-8}$ is 1 to 5; and X⁻ is a conjugated base of a Brønsted acid.

2. The fluorinated S-(perfluoroalkyl)dibenzothiophenium salt as defined in claim 1 in which Rf is trifluoromethyl (CF$_3$) group.

3. The fluorinated S-(perfluoroalkyl)dibenzothiophenium salt as defined in claim 1 in which the total number of fluorine atoms of $R^{1-8}$ is 2 to 4; or $R^2$=$R^7$=F and $R^1$=$R^3$=$R^4$=$R^5$=$R^6$=$R^8$=H; or $R^3$=$R^6$=F and $R^1$=$R^2$=$R^4$=$R^5$=$R^7$=$R^8$=H; or $R^2$=$R^5$=F and $R^1$=$R^3$=$R^4$=$R^6$=$R^7$=$R^8$=H; or $R^2$=$R^3$=$R^6$=$R^7$=F and $R^1$=$R^4$=$R^5$=$R^8$=H.

4. The fluorinated S-(perfluoroalkyl)dibenzothiophenium salt as defined in claim 1 in which X⁻ is CF$_3$SO$_3$⁻, Cl⁻, Br⁻, BF$_4$⁻, PF$_6$⁻, or HSO$_4$⁻.

5. A method of preparing fluorinated S-(perfluoroalkyl)dibenzothiophenium salt represented by the general formula (I')

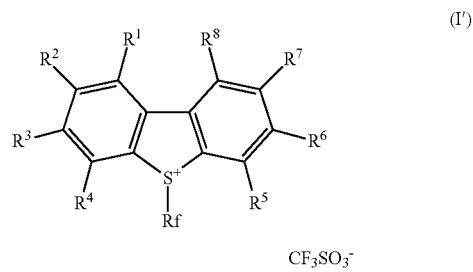

CF$_3$SO$_3$⁻

The method comprising: reacting fluorinated biphenyl represented by the general formula (II) with any combination of perfluoroalkanesulfinate salt represented by the general formula RfSO$_2$M with trifluoromethanesulfonic anhydride [(CF$_3$SO$_2$)$_2$O], trifluoromethanesulfonic acid (CF$_3$SO$_3$H), and/or carboxylic anhydride represented by the general formula (RCO)$_2$O:

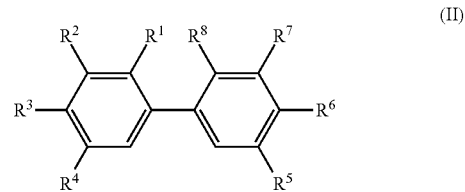

wherein Rf is a perfluoroalkyl group having 1 to 4 carbons; $R^1$, $R^2$, $R^3$, $R^4$, $R^5$, $R^6$, $R^7$ and $R^8$ each is a hydrogen atom or a fluorine atom, provided that the total number of fluorine atoms of $R^{1-8}$ is 1 to 5; M is a metal atom or an ammonium moiety; and R is an alkyl or haloalkyl group having 1 to 4 carbons.

6. The method of claim 5, wherein the method comprising: reacting the fluorinated biphenyl with the perfluoroalkanesulfinate salt and trifluoromethanesulfonic anhydride.

7. The method of claim 5, wherein the method comprising: reacting the fluorinated biphenyl with the perfluoroalkanesulfinate salt, trifluoromethanesulfonic anhydride, and the carboxylic anhydride.

8. The method of claim 5, wherein the method comprising: reacting the fluorinated biphenyl with the perfluoroalkanesulfinate salt, trifluoromethanesulfonic acid, and the carboxylic anhydride.

9. The method of claim 5, wherein the method comprising: reacting the fluorinated biphenyl with the perfluoroalkanesulfinate salt, trifluoromethanesulfonic anhydride, trifluoromethanesulfonic acid, and the carboxylic anhydride.

10. The method of claim 5, wherein the method comprising; (first step) mixing the perfluoroalkanesulfinate salt with trifluoromethanesulfonic anhydride; and (second step) mixing the fluorinated biphenyl with a mixture of the first step.

11. The method of claim 5, in which Rf is trifluoromethyl (CF$_3$) group, and the total number of the fluorine atoms of $R^{1-8}$ is 2 to 4.

12. The method of claim 5, in which the fluorinated biphenyl is the compound which is recovered by desulfurization from fluorinated dibenzothiophene represented by formula (V):

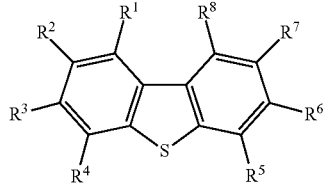

wherein $R^1$, $R^2$, $R^3$, $R^4$, $R^5$, $R^6$, $R^7$ and $R^8$ each is a hydrogen atom or a fluorine atom, provided that the total number of fluorine atoms of $R^{1-8}$ is 1 to 5.

13. The method to isolate fluorinated S-(perfluoroalkyl) dibenzothiophenium salt represented by the general formula (I'):

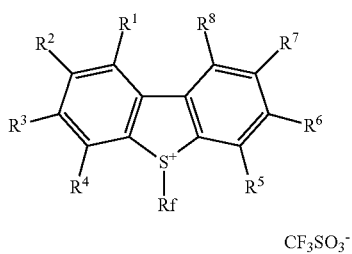

The method comprising: washing the reaction mixture resulting from the method of claim 5 with water and an organic solvent(s) which does not dissolve or scarcely dissolve fluorinated S-(perfluoroalkyl)dibenzothiophenium salt represented by the general formula (I').

14. The method to isolate fluorinated S-(perfluoroalkyl) dibenzothiophenium salt represented by the general formula (I'):

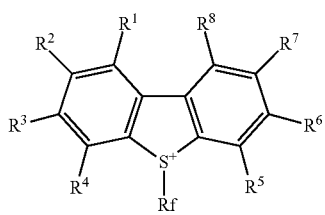

The method comprising: washing the reaction mixture resulting from the method of claim 12 with water and an organic solvent(s) which does not dissolve or scarcely dissolve fluorinated S-(perfluoroalkyl)dibenzothiophenium salt represented by the general formula (I').

15. The process of claim 13, wherein the organic solvent is selected from a group of diethyl ether, dipropyl ether, di(isopropyl) ether, dibutyl ether, di(isobutyl) ether, di(sec-butyl) ether, tert-butyl methyl ether, 1,2-dimethoxyethane, 1,2-diethoxyethane, dioxane, diglyme, ethyl acetate, propyl acetate, isopropyl acetate, ethyl propionate, dichloromethane, chloroform, carbon tetrachloride, dichloroethane, benzene, toluene, xylene, chlorobenzene, dichlorobenzene, fluorobenzene, benzotrifluoride, n-pentane and its isomers, n-hexane and its isomers, n-heptane and its isomers, and n-octane and its isomers.

16. A method of preparing fluorinated S-(perfluoroalkyl) dibenzothiophenium salt represented by the general formula (I):

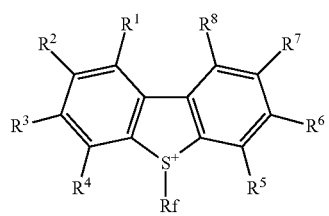

The method comprising: reacting fluorinated S-(perfluoroalkyl)dibenzothiophenium salt represented by the general formula (I''):

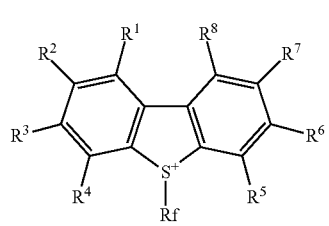

with $(M')^+X^-$, wherein Rf is a perfluoroalkyl group having 1 to 4 carbons; $R^1$, $R^2$, $R^3$, $R^4$, $R^5$, $R^6$, $R^7$ and $R^8$ each is a hydrogen atom or a fluorine atom, provided that the total number of fluorine atoms of $R^{1-8}$ is 1 to 5; M' is a hydrogen atom, a metal atom, or an ammonium moiety; and $X^-$ and $(X')^-$ each is a conjugated base of Brønsted acid, provided that $X^-$ and $(X')^-$ are different.

17. A method of claim 16, in which M' is H, Li, Na, K, or Ag, and X' is $CF_3SO_3$, Cl, Br, or $HSO_4$.

18. Fluorinated 2-[(perfluoroalkyl)sulfinyl]biphenyl represented by the following general formula (IV):

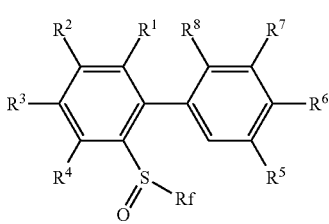

wherein Rf is a perfluoroalkyl group having 1 to 4 carbons; $R^1$, $R^2$, $R^3$, $R^4$, $R^5$, $R^6$, $R^7$ and $R^8$ each is a hydrogen atom or a fluorine atom, provided that the total number of fluorine atoms of $R^{1-8}$ is 1 to 5.

19. The fluorinated 2-[(perfluoroalkyl)sulfinyl]biphenyl as defined in claim 18 in which Rf is trifluoromethyl ($CF_3$) group.

20. The fluorinated 2-[(perfluoroalkyl)sulfinyl]biphenyl as defined in claim 18 in which the total number of fluorine atoms is 2-4.

* * * * *